United States Patent
Stoddart et al.

(10) Patent No.: US 10,745,418 B2
(45) Date of Patent: Aug. 18, 2020

(54) SUPRAMOLECULAR ASSEMBLY OF RIGID MACROCYCLES THROUGH COOPERATIVE HYDROGEN BOND INTERACTIONS

(71) Applicant: Northwestern University, Evanston, IL (US)

(72) Inventors: James Fraser Stoddart, Evanston, IL (US); Zhichang Liu, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 16/069,940

(22) PCT Filed: Jan. 13, 2017

(86) PCT No.: PCT/US2017/013301
§ 371 (c)(1),
(2) Date: Jul. 13, 2018

(87) PCT Pub. No.: WO2017/123843
PCT Pub. Date: Jul. 20, 2017

(65) Prior Publication Data
US 2019/0016738 A1    Jan. 17, 2019

Related U.S. Application Data

(60) Provisional application No. 62/278,200, filed on Jan. 13, 2016.

(51) Int. Cl.
*C07D 519/00* (2006.01)
*C07D 471/06* (2006.01)
*H01M 10/052* (2010.01)

(52) U.S. Cl.
CPC ......... *C07D 519/00* (2013.01); *C07D 471/06* (2013.01); *H01M 10/052* (2013.01)

(58) Field of Classification Search
CPC .................................................. C07D 471/06
See application file for complete search history.

(56) References Cited

U.S. PATENT DOCUMENTS

| 9,546,169 | B2 * | 1/2017 | Stoddart | .............. | C07D 471/06 |
| 2016/0130271 | A1 | 5/2016 | Stoddart | | |
| 2016/0276669 | A1 | 9/2016 | Chen | | |

OTHER PUBLICATIONS

Hoger. Chemistry: A European Journal, 2004, 10, 1320-29 (Year: 2004).*
Wu. Angewandte Chemie International Edition, 2015, 54, 11971-11977, first published Aug. 20, 2015 (Year: 2015).*
Au-Yeung. Chemical Communications, 2009, 419-421, supporting information pp. S1-S23 (Year: 2009).*
Aggeli, A., et al. "Hierarchical self-assembly of chiral rod-like molecules as a model for peptide β-sheet tapes, ribbons, fibrils, and fibers." Proceedings of the National Academy of Sciences 98.21 (2001): 11857-11862.
Aida, T., et al. "Functional supramolecular polymers." Science 335.6070 (2012): 813-817.
Ajami, D. et al. "More chemistry in small spaces." Accounts of chemical research 46.4 (2012): 990-999.
Ajami, D. et al. "Soft templates in encapsulation complexes." Chemical Society Reviews 44.2 (2014): 490-499.
Beijer, F. H., et al. "Self-complementarity achieved through quadruple hydrogen bonding." Angewandte Chemie International Edition 37.1-2 (1998): 75-78.
Blight, B. A., et al. "An AAAA—DDDD quadruple hydrogen-bond array." Nature chemistry 3.3 (2011): 244.
Borges, A. R., et al. "Self-assembled thermoreversible gels of nonpolar liquids by racemic propargylic alcohols with fluorinated and nonfluorinated aromatic rings." Langmuir 24.14 (2008): 7421-7431.
Brizard, A., et al. "Chirality effects in self-assembled fibrillar networks." Low Molecular Mass Gelator. Springer, Berlin, Heidelberg, 2005. 167-218.
Caplar, Vesna, et al. "Positionally Isomeric Organic Gelators: Structure—Gelation Study, Racemic versus Enantiomeric Gelators, and Solvation Effects." Chemistry—A European Journal 16.10 (2010): 3066-3082.
Corbin, Perry S., et al. "Self-association without regard to prototropy. A heterocycle that forms extremely stable quadruply hydrogen-bonded dimers." Journal of the American Chemical Society 120.37 (1998): 9710-9711.
Desiraju, G. R. "The C—H—O hydrogen bond: structural implications and supramolecular design." Accounts of Chemical Research 29.9 (1996): 441-449.
Desiraju, G. R. "Distinction between the weak hydrogen bond and the van der Waals interaction." Chemical Communications 8 (1998): 891-892.
Edwards, W. et al. "Enantioselective component selection in multicomponent supramolecular gels." Journal of the American Chemical Society 136.3 (2014): 1116-1124.
Fischer, Lucile, et al. "Control of Duplex Formation and Columnar Self-Assembly with Heterogeneous Amide/Urea Macrocycles." Angewandte Chemie International Edition 48.9 (2009): 1625-1628.
Fleming, S. et al. "Design of nanostructures based on aromatic peptide amphiphiles." Chemical Society Reviews 43.23 (2014): 8150-8177.
Frederix, Pim WJM, et al. "Exploring the sequence space for (tri-) peptide self-assembly to design and discover new hydrogels." Nature chemistry 7.1 (2015): 30.

(Continued)

*Primary Examiner* — Noble E Jarrell
(74) *Attorney, Agent, or Firm* — Quarles & Brady LLP

(57) ABSTRACT

Provided herein are supramolecular assemblies, the supramolecular assemblies comprising a racemic mixture of rigid macrocycles capable of interacting through [C—H . . . O] hydrogen bonds. Also provided herein are methods for preparing supramolecular assemblies, the method comprising providing a mixture of rigid macrocycles capable of interacting through [C—H . . . O] hydrogen bonds, the mixture of rigid macrocycles comprising a first rigid macrocycle enantiomer and a second rigid macrocycle enantiomer, and providing a solvent.

20 Claims, 12 Drawing Sheets

(56) References Cited

OTHER PUBLICATIONS

Frkanec, L. et al. "Chiral bis (amino acid)- and bis (amino alcohol)-oxalamide gelators. Gelation properties, self-assembly motifs and chirality effects." Chemical communications 46.4 (2010): 522-537.
Gabutti, Sandro, et al. "A rigid sublimable naphthalenediimide cyclophane as model compound for UHV STM experiments." Chemical Communications 20 (2008): 2370-2372.
George, M. et al. "Molecular organogels. Soft matter comprised of low-molecular-mass organic gelators and organic liquids." Accounts of chemical research 39.8 (2006): 489-497.
Gong, Han-Yuan, et al. "A 'Texas-sized' molecular box that forms an anion-induced supramolecular necklace." Nature chemistry 2.5 (2010): 406.
Grimme, Stefan. "Semiempirical GGA-type density functional constructed with a long-range dispersion correction." Journal of computational chemistry 27.15 (2006): 1787-1799.
Hasell, Tom, et al. "Porous organic cage nanocrystals by solution mixing." Journal of the American Chemical Society 134.1 (2011): 588-598.
He, Yabing, et al. "Self-discriminating and hierarchical assembly of racemic binaphthyl-bisbipyridines and silver ions: from metal-locycles to gel nanofibers." Chemical Communications 47.5 (2011): 1589-1591.
Hennig, Andreas, et al. "Anion-Macrodipole Interactions: Self-Assembling Oligourea/Amide Macrocycles as Anion Transporters that Respond to Membrane Polarization." Journal of the American Chemical Society 131.46 (2009): 16889-16895.
Huang, Zhegang, et al. "Pulsating tubules from noncovalent macrocycles." Science 337.6101 (2012): 1521-1526.
Hwang, Ilha, et al. "Cucurbit [7] uril: A Simple Macrocyclic, pH-Triggered Hydrogelator Exhibiting Guest-Induced Stimuli-Responsive Behavior." Angewandte Chemie International Edition 46.1-2 (2007): 210-213.
International Searching Authority, International Search Report and Written Opinion for application PCT/US2017/013301, 13 pages, dated Apr. 4, 2017.
Jung, Jong Hwa, et al. "Creation of both right-handed and left-handed silica structures by sol-gel transcription of organogel fibers comprised of chiral diaminocyclohexane derivatives." Journal of the American Chemical Society 122.20 (2000): 5008-5009.
Kang, Jiheong, et al. "A rational strategy for the realization of chain-growth supramolecular polymerization." Science 347.6222 (2015): 646-651.
Kar, T. et al. "Comparison of cooperativity in CH . . . O and OH . . . O hydrogen bonds." The Journal of Physical Chemistry A 108.42 (2004): 9161-9168.
Koshkakaryan, G., et al. "Multilayered nanofibers from stacks of single-molecular thick nanosheets of hexakis (alkoxy) triphenylenes." Chemical Communications 46.45 (2010): 8579-8581.
Kouwer, Paul HJ, et al. "Responsive biomimetic networks from polyisocyanopeptide hydrogels." Nature 493.7434 (2013):651.
Kumari, H. et al. "Solution structures of nanoassemblies based on pyrogallol [4] arenes." Accounts of chemical research 47.10 (2014): 3080-3088.
Kumari, H., et al. "Magnetic differentiation of pyrogallol [4] arene tubular and capsular frameworks." Journal of the American Chemical Society 135.19 (2013): 7110-7113.
Lafitte, V. GH, et al. "Quadruply hydrogen bonded cytosine modules for supramolecular applications." Journal of the American Chemical Society 128.20 (2006): 6544-6545.
Lin, Jianbin, et al. "Homochiral and heterochiral assembly preferences at different length scales—conglomerates and racemates in the same assemblies." Chemical Communications 49.81 (2013): 9320-9322.
Liu, Simin, et al. "Guest packing motifs within a supramolecular nanocapsule and a covalent analogue." Journal of the American Chemical Society 135.11 (2013): 4314-4324.
Liu, Yuzhou, et al. "Supramolecular Archimedean cages assembled with 72 hydrogen bonds." Science 333.6041 (2011): 436-440.
Liu, Z., et al. "Assembly of supramolecular nanotubes from molecular triangles and 1, 2-dihalohydrocarbons." Journal of the American Chemical Society 136.47 (2014): 16651-16660.
Makarevic, Janja, et al. "Chiral bis (amino alcohol) oxalamide gelators—gelation properties and supramolecular organization: racemate versus pure enantiomer gelation." Chemistry—A European Journal 9.22 (2003): 5567-5580.
Meazza, Lorenzo, et al. "Halogen-bonding-triggered supramolecular gel formation." Nature chemistry 5.1 (2013): 42.
Montenegro, J. et al. "Ion channel models based on self-assembling cyclic peptide nanotubes." Accounts of chemical research 46.12 (2013): 2955-2965.
Morris, Kyle L., et al. "Chemically programmed self-sorting of gelator networks." Nature communications 4 (2013): 1480.
Nagy, Katelyn J., et al. "Enhanced mechanical rigidity of hydrogels formed from enantiomeric peptide assemblies." Journal of the American Chemical Society 133.38 (2011): 14975-14977.
Nalluri, Siva Krishna Mohan, et al. "Biocatalytic Self-Assembly of Supramolecular Charge-Transfer Nanostructures Based on n-Type Semiconductor-Appended Peptides." Angewandte Chemie International Edition 53.23 (2014): 5882-5887.
Ogi, Soichiro, et al. "Mechanism of self-assembly process and seeded supramolecular polymerization of perylene bisimide organogelator." Journal of the American Chemical Society 137.9 (2015): 3300-3307.
Pantos, G. D. et al. "Hydrogen-Bonded Helical Organic Nanotubes." Angewandte Chemie International Edition 46.1-2 (2007): 194-197.
Park, Daniel J., et al. "Plasmonic photonic crystals realized through DNA-programmable assembly." Proceedings of the National Academy of Sciences 112.4 (2015): 977-981.
Perdew, J. P. et al "Generalized gradient approximation made simple." Physical review letters 77.18 (1996): 3865.
Piana, Francesca, et al. "Organophosphorus chemical warfare agent simulant DMMP promotes structural reinforcement of urea-based chiral supramolecular gels." RSC Advances 5.16 (2015): 12287-12292.
Raeburn, J. et al. "Multicomponent low molecular weight gelators." Chemical Communications 51.25 (2015): 5170-5180.
Raeburn, J. et al. "The importance of the self-assembly process to control mechanical properties of low molecular weight hydrogels." Chemical Society Reviews 42.12 (2013): 5143-5156.
Rambo, Brett M., et al. "The "Texas-sized" molecular box: A versatile building block for the construction of anion-directed mechanically interlocked structures." Accounts of chemical research 45.8 (2012): 1390-1401.
Ren, Changliang, et al. "Five-fold-symmetric macrocyclic aromatic pentamers: high-affinity cation recognition, ion-pair-induced columnar stacking, and nanofibrillation." Journal of the American Chemical Society 133.35 (2011): 13930-13933.
Roche, C., et al. "Homochiral columns constructed by chiral self-sorting during supramolecular helical organization of hat-shaped molecules." Journal of the American Chemical Society 136.19 (2014): 7169-7185.
Scheiner, Steve. "The CH? O H-Bond as a Determining Factor in Molecular Structure." Noncovalent Forces. Springer, Cham, 2015. 69-105.
Schneebeli, S. T., et al. "Electron sharing and anion—pi recognition in molecular triangular prisms." Angewandte Chemie International Edition vol. 52 (2013).
Shao, Yihan, et al. "Advances in molecular quantum chemistry contained in the Q-Chem 4 program package." Molecular Physics 113.2 (2015): 184-215.
Shen, Z. et al. "Tuning the gelation ability of racemic mixture by melamine: enhanced mechanical rigidity and tunable nanoscale chirality." Langmuir 30.35 (2014): 10772-10778.
Smith, David K. "Lost in translation? Chirality effects in the self-assembly of nanostructured gel-phase materials." Chemical Society Reviews 38.3 (2009): 684-694.
Steed, J. W. "Anion-tuned supramolecular gels: a natural evolution from urea supramolecular chemistry." Chemical Society Reviews 39.10 (2010): 3686-3699.
Steed, J. W. "Supramolecular gel chemistry: developments over the last decade." Chemical Communications 47.5 (2011): 1379-1383.

(56) References Cited

OTHER PUBLICATIONS

Steiner, Thomas. "Unrolling the hydrogen bond properties of C—H—O interactions." Chemical Communications 8 (1997):727-734.
Terech, P. et al. "Low molecular mass gelators of organic liquids and the properties of their gels." Chemical reviews 97.8 (1997): 3133-3160.
Van Esch, J. H., et al. "New functional materials based on self-assembling organogels: from serendipity towards design." Angewandte Chemie International Edition 39.13 (2000): 2263-2266.
Watanabe, Y. et al. "Diastereomixture and Racemate of m yo-Inositol Derivatives, Stronger Organogelators than the Corresponding Homochiral Isomers." Organic letters 6.10 (2004): 1547-1550.
Weiss, Richard G. "The past, present, and future of molecular gels. What is the status of the field, and where is it going?." Journal of the American Chemical Society 136.21 (2014): 7519-7530.
Wu, Xiangxiang, et al. "Discrete Stacking of Aromatic Oligoamide Macrocycles." Journal of the American Chemical Society 137.18 (2015): 5879-5882.
Yamagishi, Hiroshi, et al. "Metal—Organic Nanotube with Helical and Propeller-Chiral Motifs Composed of a C 10-Symmetric Double-Decker Nanoring." Journal of the American Chemical Society 137.24 (2015): 7628-7631.
Zhang, Zibin, et al. "Formation of Linear Supramolecular Polymers That Is Driven by C? H—p Interactions in Solution and in the Solid State." Angewandte Chemie International Edition 50.6 (2011): 1397-1401.

\* cited by examiner

SUPRAMOLECULAR ASSEMBLY OF RIGID MACROCYCLES THROUGH COOPERATIVE HYDROGEN BOND INTERACTIONS

CROSS-REFERENCE TO RELATED APPLICATIONS

This patent application is a national stage filing under 35 U.S.C. 371 of International Application No. PCT/US2017/013301, filed Jan. 13, 2017, which claims the benefit of priority of U.S. Provisional Patent Application Ser. No. 62/278,200, filed 13 Jan. 2016, both of which are incorporated herein by reference in their entirety.

FIELD OF INVENTION

The invention generally relates to supramolecular assemblies. In particular, the invention relates to supramolecular assembly of rigid macrocycles through cooperative [C—H . . . O] interactions.

BACKGROUND

Low-molecular-weight gelators (LMWGs) are capable of assembling into interwoven fibrillar networks that entrap solvents between strands to form thermoreversible supramolecular gels.[1-10] Chirality has a profound influence on the macroscopic gelation of solvents by facilitating the growth and stabilization of noncovalent helical fibers as well as their interwoven networks, often driven by stereogenic centers present in the molecular structures of chiral LMWGs.[11-13] As a consequence, most of the highly efficient LMWGs, exhibiting strong gelling ability, are composed of enantiomerically pure chiral molecules.[1, 14-16] Generally speaking, the corresponding racemates of these enantiopure chiral gelators, either do not form gels or occasionally form only weak ones that transform readily into precipitates or discrete crystals.[12, 17, 18] The opposite situation, in which a racemate generates a gel, while both its enantiomers are less efficient gelators, or even lack any gelling ability at all, is rare. Although there are a few examples of gels resulting from the assembly of racemic gelators incorporating flexible structures, driven by means of various noncovalent bonding interactions, gels assembled from highly rigid racemic gelators at the behest of multiple weak [C—H . . . O] interactions as the major driving force remain unexplored to the best of our knowledge.[18-26, 27] Kim et al. have reported that rigid achiral cucurbit[7]uril (CB[7]) can act as a hydrogelator, but only in the presence of mineral acids.[28] The relationship between stereochemistry and gelation, however, has yet to be fully elucidated.

Hydrogen-bonding arrays are well-established modules for the formation of biotic and abiotic supramolecular polymers, as well as for the assembly of cylindrical and spherical capsules.[29, 30, 31-36] While a number of planar quadruple hydrogen-bonding motifs give rise to supramolecular arrays, cyclic peptides are amongst the few well-known examples of multiple hydrogen-bonding ring motifs that lead to the formation of supramolecular nanotubes.[37-43] Also, despite the remarkable progress that has been made in recent years, interactions involving hydrogen-bonding motifs have been restricted for the most part to the use of [O—H . . . O] and [N—H . . . O] noncovalent bonds because of their greater strengths and propensities to act cooperatively. [29, 30, 41, 44-49] These strong noncovalent bonds facilitate the construction of well-defined supramolecular assemblies by over-riding the influence of other competing interactions from mismatched molecular structures, counter ions and solvents. Permutations of hydrogen bonds composed of multiple intermolecular cooperative [C—H . . . O] interactions, leading to the formation of supramolecular assemblies, have remained largely out of reach on account of the relative weakness of single [C—H . . . O] interactions.[49]

There are a number of applications for the supramolecular assemblies. For example, supramolecular assemblies may be used to prepare batteries, organic semiconductors, including but not limited to organic field effect transistors, organic light emitting diodes, and photovoltaic devices, membranes, fibrous networks, or gas sensors. As a result, there is a need for new supramolecular assemblies.

SUMMARY OF THE INVENTION

One aspect of the invention is a supramolecular assembly, the supramolecular assembly comprising a racemic mixture of rigid macrocycles capable of interacting through [C—H . . . O] hydrogen bonds. The mixture may be a racemic mixture of a first rigid macrocycle enantiomer and a second rigid macrocycle enantiomer. In some embodiments, the mixture of rigid macrocycles comprises a first rigid triangular macrocycle enantiomer and a second rigid triangular macrocycle enantiomer. In some embodiments, the first rigid macrocycle enantiomer is a rigid napthalenediimide-based macrocycle enantiomer or a derivative thereof and the second rigid macrocycle enantiomer is a rigid napthalenediimide-based macrocycle enantiomer or a derivative thereof. In particular embodiments, the first rigid napthalenediimide-based macrocycle enantiomer is the compound of:

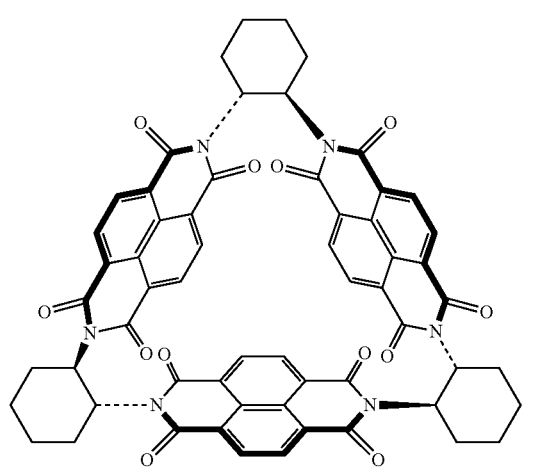

Formula (I)

or a derivative thereof and the second rigid napthalenediimide-based macrocycle enantiomer is a compound of:

Formula (II)

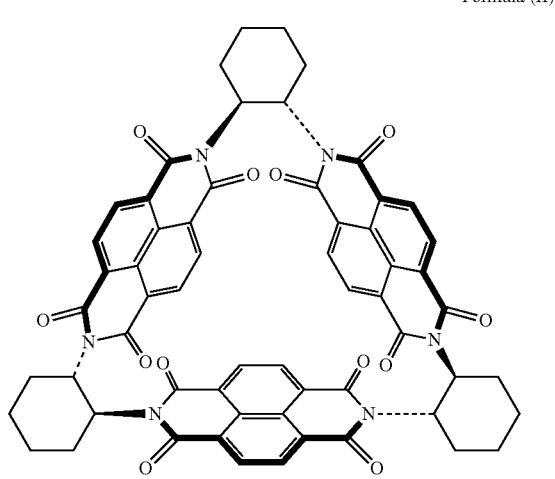

or a derivative thereof. The first rigid macrocycle enantiomer may cooperatively interact with the second rigid macrocycle enantiomer through [C—H . . . O] hydrogen bonds. The first rigid macrocycle enantiomer and the second rigid macrocycle enantiomer may coaxially stack in an alternating fashion.

In some embodiments, the supramolecular assemblies may be a gel or precipitate. The supramolecular assemblies may have a fibrillar morphology or a needle morphology. The supramolecular assemblies may have a high-aspect ration. In particular embodiments, the supramolecular assembly has a first dimension of less than about 3 nm and a second dimension of greater than about 100 nm.

In another aspect of the invention is a method for preparing a supramolecular assembly, the method comprising providing a mixture of rigid macrocycles capable of interacting through [C—H . . . O] hydrogen bonds, the mixture of rigid macrocycles comprising a first rigid macrocycle enantiomer and a second rigid macrocycle enantiomer, and providing a solvent. In some embodiments, the mixture of rigid macrocycles is an equimolar mixture of the first rigid macrocycle and the second rigid macrocycle. In some embodiments, providing the mixture of rigid macrocycles comprises mixing a first solution, the first solution comprising the first rigid macrocycle, and a second solution, the second solution comprising the second rigid macrocycle. In some embodiments, providing the mixture of rigid macrocycles comprises dissolving the first rigid macrocycle and/or the second rigid macrocycle. In some embodiments, the solvent is a halogenated alkane. In particular embodiments, the solvent comprises a member selected from the group consisting of $CH_2Cl_2$, $CHCl_3$, $ClCH_2CH_2Cl$, $ClCH_2CH_2Br$, $ClCH_2CH_2I$, $BrCH_2CH_2Br$, and any combination thereof.

Another aspect of the invention is devices comprising the supramolecular assemblies described herein. In some embodiments, the device is a battery. In particular embodiments, the batter is a lithium batter. In some embodiments, the device is an organic semiconductor device. In particular embodiments, the organic semiconductor device is a photvoltaic device, an organic field effect transistor, an organic light emitting diode. In some embodiments, the device is a membrane or a fibrous network. In some embodiments, the device is a gas sensor comprising a membrane comprised the supramolecular assemblies.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

DETAILED DESCRIPTION

Figure 1A:
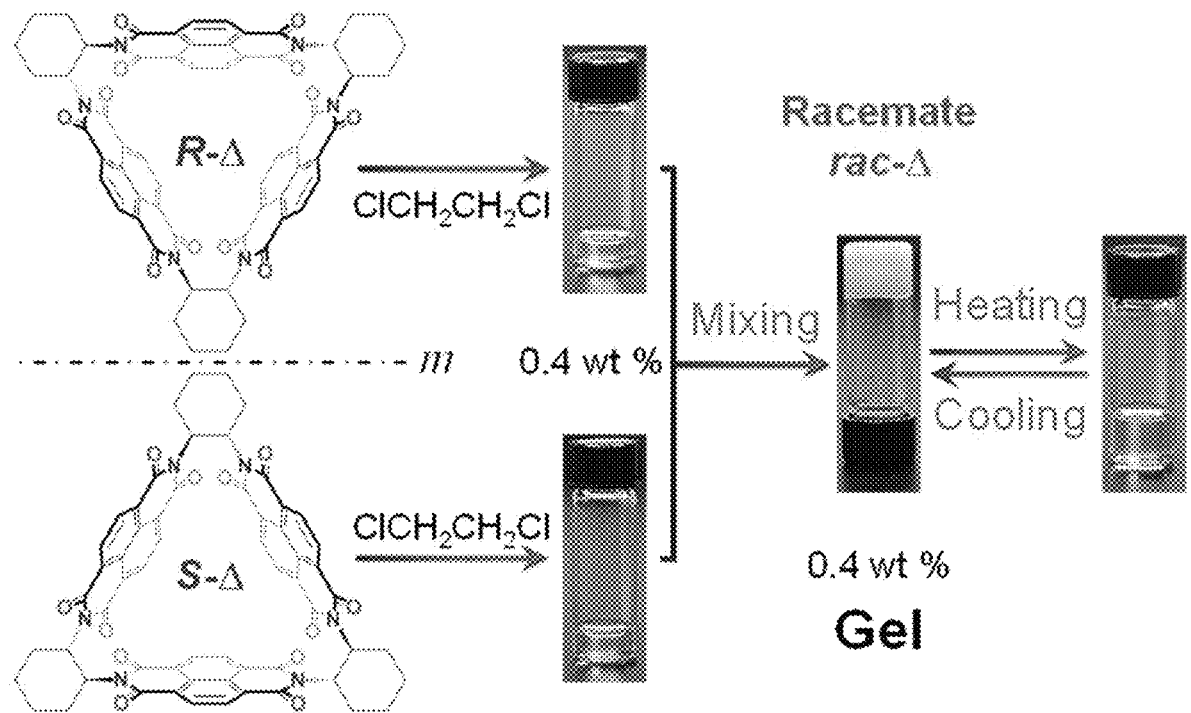
FIG. 1A. shows structural formulae of R-Δ and S-Δ, followed by photographs of the formation of thermoreversible gels from the racemate rac-Δ by mixing R-Δ and S-Δ in $ClCH_2CH_2Cl$ at a 1:1 molar ratio in concentrations of 0.4 wt %.

Disclosed herein are supramolecular assemblies that spontaneously form through the cooperative [C—H ... O] hydrogen bonds. Although supramolecular assemblies have been previously described that exploit strong hydrogen bond, e.g., [O—H ... O] or [N—H ... O], it is surprising that the week [C—H ... O] hydrogen bond can drive supramolecular assembly. Moreover, the supramolecular assemblies described herein spontaneously form from a mixture of enantiomers.

An aspect of the invention is a supramolecular assembly. The supramolecular assembly comprises a mixture of rigid macrocycles capable of interacting through [C—H ... O] hydrogen bonds. Rigid macrocycles are cyclic macromolecules or a macromolecular cyclic portion of a molecule that is constrained against large-amplitude conformational rearrangement around the cyclic portion of the molecule. Rigid macrocycles may be composed of one or more subunits arranged in a cyclic manor. In certain embodiments, the rigid macrocycle is composed of two or more subunits. In particular embodiments, the rigid macrocycle is composed of two alternating subunits.

The rigid macrocycles may be rigid, triangular naphthalenediimide-based macrocycles. Examples of rigid, triangular naphthalenediimide-based macrocycles macrocycles are provided in Formulas (I) and (II).

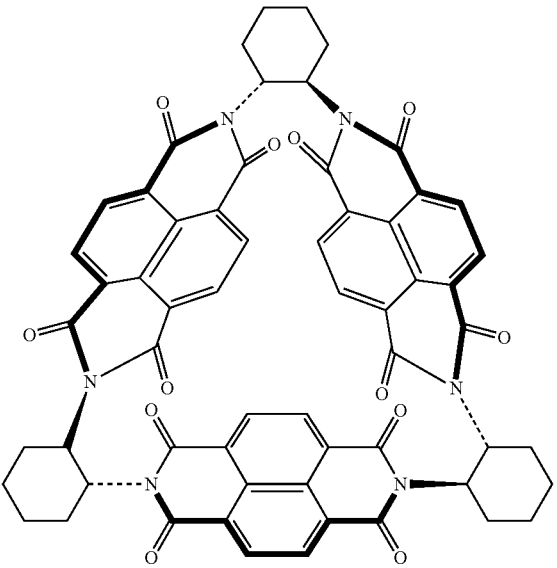

Formula (I)

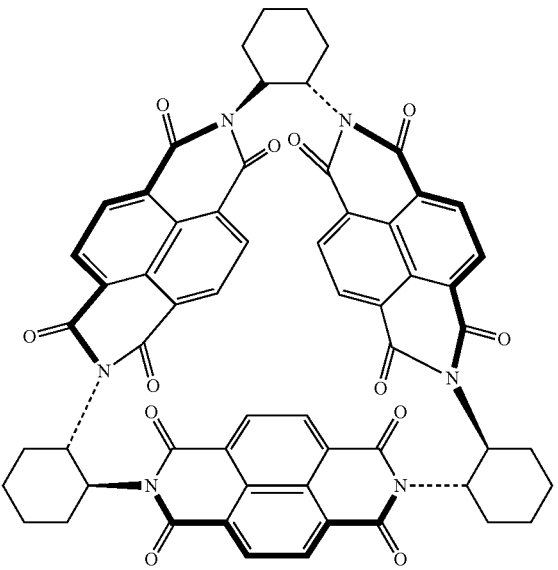

Formula (II)

The compounds of Formulas (I) and (II) each comprise an alternating cyclic arrangement of naphthalenediimide moieties and cycloalkane moieties. The compound of Formula (I) is sometimes referred to as (RRRRRR)-NDI-Δ, R-Δ, or (−)-NDI-Δ. The compound of Formula (II) is sometimes referred to as (SSSSS)-NDI-Δ, S-Δ, or (+)-NDI-Δ.

The rigid macrocycles may also be derivatives of R-Δ and S-Δ. Derivatives of R-Δ and S-Δ may include cyclohexane moieties where one or more hydrogen atoms at any of positions 1-6 of the cyclohexane moiety are substituted. Substituents may include hydrocarbon moieties, halogen moieties, oxygen-containing moieties, nitrogen-containing moieties, sulfur containing moieties, or combinations thereof. In certain embodiments, substituents may be $C_{1-6}$ alkyl moieties, $C_{1-6}$ alkenyl moieties, $C_{1-6}$ alkynyl moieties, phenyl moieties, halo moieties, $C_{0-6}$ hydroxyl moieties, $C_{1-6}$ ether moieties, $C_{1-6}$ carbonyl moieties, $C_{1-6}$ aldehyde moieties, $C_{1-6}$ carboxyl moieties, $C_{1-6}$ ester moieties, or combinations thereof.

Derivatives of R-Δ and S-Δ may include $C_{3-5}$ cycloalkane moieties or $C_{7-8}$ cycloalkane moieties that also have (RR) or (SS) distereoisomer centers in replace of the cyclohexane moieties. Derivatives of this type also includes substituted $C_{3-5}$ cycloalkane moieties or $C_{7-8}$ cycloalkane moieties where one or more hydrogen atoms at any position are substituted. Substituents may include hydrocarbon moieties, halogen moieties, oxygen-containing moieties, nitrogen-containing moieties, sulfur containing moieties, or combinations thereof. In certain embodiments, substituents may be $C_{1-6}$ alkyl moieties, $C_{1-6}$ alkenyl moieties, $C_{1-6}$ alkynyl moieties, phenyl moieties, halo moieties, $C_{0-6}$ hydroxyl moieties, $C_{1-6}$ ether moieties, $C_{1-6}$ carbonyl moieties, $C_{1-6}$ aldehye moieties, $C_{1-6}$ carboxyl moieties, $C_{1-6}$ ester moieties, or combinations thereof.

Derivatives of R-Δ and S-Δ may include moieties that are not cycloalkanes that also have (RR) or (SS) distereoisomer centers in replace of the cyclohexane moieties.

The naphthalenediimide-based triangular compounds R-Δ and S-Δ may be synthesized and scaled using the protocol outlined in Angew. Chem. Int. Ed. 2013, 52, 13100-13104 or U.S. Pat. Pub. No. 2016/0276669; herein incorporated by reference in their entirety. Briefly, each of R-Δ and S-Δ may be prepared from a single-step condensation of the appropriate (RR)- or (SS)-trans-1,2-diaminocyclohexane with naphthalenetetracarboxylic dianhydride. Derivatives of each of R-Δ and S-Δ may also be prepared from the substituted (RR)- or (SS)-trans-1,2-diaminocyclohexane with naphthalenetetracarboxylic dianhydride. Derivatives of each of R-Δ and S-Δ may also be prepared from (RR)- or (SS)-trans-1,2-diaminocyclopentane or substituted (RR)- or (SS)-trans-1,2-diaminocyclopentane with naphthalenetetracarboxylic dianhydride.

The supramolecular assemblies may comprise a mixture of enantiomers. In certain embodiments, the mixture may comprise a mole ratio of between 60:40 to 40:60 of a first enantiomer to a second enantiomer, including any mole ratio in between. Particular embodiments, are comprised of racemic mixtures having an equimolar ratio of the first enantiomer to the second enantiomer. The first enantiomer and the second enantiomer may be rigid, triangular macrocycle enantiomers. In particular embodiments, the rigid, triangular macrocycle enantiomers are R-Δ or a derivative thereof and S-Δ or a derivative thereof.

In certain embodiments, the supramolecular assembly is a gel. In other embodiments, the supramolecular assembly is a precipitate.

In certain embodiments, the supramolecular assembly has a fibrillar morphology or a needle morphology. In certain embodiments, the supramolecular assembly has a high-aspect ratio. In certain embodiments, the supramolecular assembly has a first dimension of less than about 3 nm and a second dimension of greater than about 100 nm.

Another aspect of the invention is a method for preparing supramolecular assemblies. The method for preparing a supramolecular assembly comprises providing a mixture of rigid macrocycles capable of interacting through [C—H . . . O] hydrogen bonds, the mixture of rigid macrocycles comprising a first rigid macrocycle enantiomer and a second rigid macrocycle enantiomer, and providing a solvent. In certain embodiments, the mixture of rigid macrocycles is an equimolar mixture of the first rigid macrocycle and the second rigid macrocycle. In some embodiments, providing the mixture of rigid macrocycles comprises mixing a first solution, the first solution comprising the first rigid macrocycle, and a second solution, the second solution comprising the second rigid macrocycle. In other embodiments, providing the mixture of rigid macrocycles comprises dissolving the first rigid macrocycle and/or the second rigid macrocycle.

The solvent to be used in the method solvent may be a halogenated alkane. In certain embodiments, the solvent comprises a member selected from the group consisting of $CH_2Cl_2$, $CHCl_3$, $ClCH_2CH_2Cl$, $ClCH_2CH_2Br$, $ClCH_2CH_2I$, $BrCH_2CH_2Br$, and any combination thereof.

There are a number of applications for the supramolecular assemblies provided herein. Batteries may be prepared with the supramolecular assemblies described herein. In some embodiments, the supramolecular assemblies may be used to prepare cathode materials for batteries or cathode components of the batteries. In particular embodiments, the batteries are lithium batteries. Use of rigid, macrocyclic compounds for use in the preparation of batteries, battery materials, or battery components are described U.S. Pat. Pub. No. 2016/027669, incorporated herein by reference in its entirety.

Organic semiconductor devices may be prepared with the supramolecular assemblies described herein. For example, the organic semiconductor device may be a photovoltaic device, an organic field effect transistor (OFETs), or an organic light emitting diodes (OLEDs). The supramolecular assembly may be used as an organic semiconductor in the preparation of an OFET. The supramolecular assembled used as an organic semiconductor will be in contact with an OFET source, an OFET drain, and a dialectric material, and the OFET will further comprise a gate to control the electrical flow in the OFET.

Moreover, membranes and fibrous networks may also be prepared with the supramolecular assemblies described herein. These membranes and fibrous networks may be used to prepare gas sensors, particularly for a reductive gas. Examples of reductive gases include, but are not limited to gaseous amines such as $NH_3$ and $NH_2NH_2$. Membranes or fibrous networks may be prepared by applying the supramolecular assemblies to a surface, drying the supramolecular assemblies, and connecting the dried membrane or fibrous network to electrodes and a sensor. When a reductive gas contacts the membrane or fibrous network, a detectable electrical signal will allow for the determination of the presence of the reductive gas.

Gelation and Precipitation of rac-Δ.

Herein, we report an example of circular [C—H . . . O] interaction-driven supramolecular gelation and precipitation that occurs (FIG. 1A) upon mixing equimolar amounts of the enantiomeric naphthalenediimide-based rigid triangular macrocycles (NDI-Δ)—namely, R-Δ and S-Δ. It relies on the formation of one-dimensional (1D) fibers brought about by the coaxial stacking assembly of R-Δ and S-Δ in an alternating fashion, driven predominantly by rings of multiple weak [C—H . . . O] interactions acting cooperatively at the interfaces between R-Δ and S-Δ. DFT Calculations reveal that the energetically more favorable stereochemical match between R-Δ and S-Δ allows them to act as two complementary double-faced 12-point [C—H . . . O] hydrogen-bonded circular arrays with an unprecedented and uninterrupted ADDAADDAADDA•DAADDAADDAAD hydrogen-bonding sequence. As a consequence, this strategy reinforces the strength and facilitates the cooperativity and linear directionality of 12 circular [C—H . . . O] interactions between R-Δ and S-Δ so as to drive the 1D supramolecular assembly of the racemate rac-Δ of R-Δ and S-Δ to form organogels.

Recently, we have demonstrated that both R-Δ and S-Δ exhibit solvent-dependent crystallization in common halogenated solvents.[51, 52] In the cases of $CH_2Cl_2$ and $CHCl_3$, R-Δ and S-Δ crystallize as non-tubular superstructures.[51] In the cases of 1,2-dihaloethanes (DXEs), however, R-Δ and S-Δ form two types of tubular superstructures—(i) single-handed helical tetrameric nanotubes in $ClCH_2CH_2Cl$ (DCE) and (ii) infinite non-helical nanotubes in $ClCH_2CH_2Br$ (CBE), $ClCH_2CH_2I$ (CIE), and $BrCH_2CH_2Br$ (DBE)—as a result of the columnar stacking of NDI-Δ with a 60° rotational angle driven by means of multiple weak [C—H . . . O] interactions acting cooperatively, in conjugation with directed halogen (X) bonding interactions along the [X . . . X]-bonded DXE chains inside the nanotubes.[52] The constitutions of the coaxially aligned DXEs play a role in templating the self-assembly of NDI-Δ into tubular superstructures.

Figure 1B:
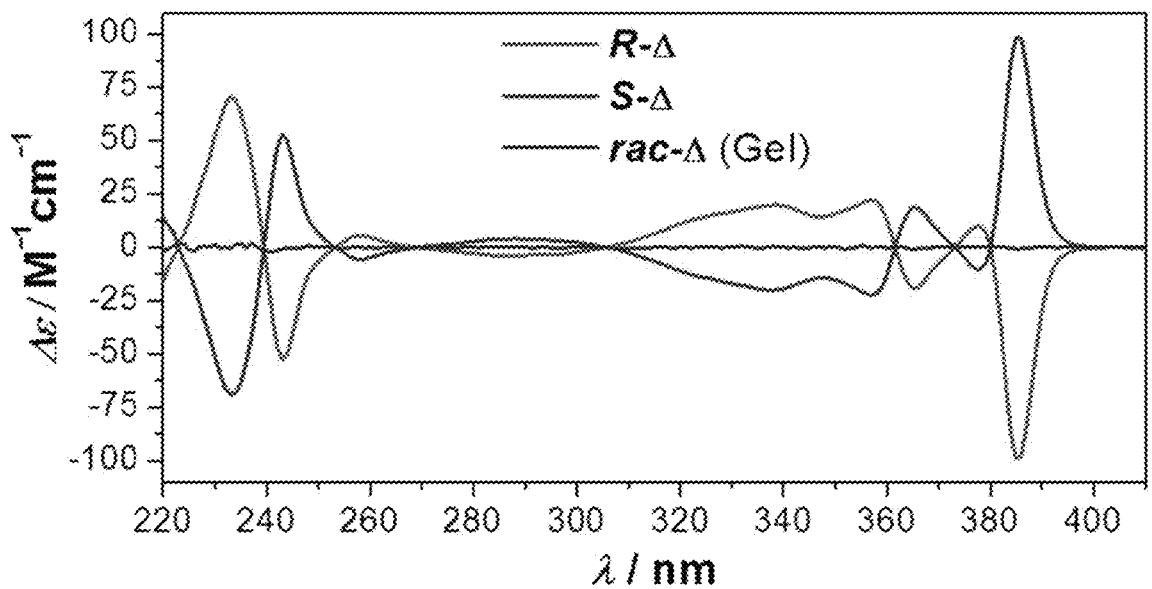
FIG. 1B shows a circular dichroism spectra of R-Δ and S-Δ in addition to the redissolved racemate rac-A, which is obtained by centrifugation of the gel, in $ClCH_2CH_2Cl$.

In an attempt to explore the role of these solvents in the assembly of the racemate rac-Δ of R-Δ and S-Δ, we discovered serendipitously that, upon mixing together equimolar solutions of R-Δ and S-Δ in DCE, a self-supporting gel is formed (FIG. 1A) within minutes. It should be emphasized that, despite the fact that the solubilities of enantiopure R-Δ and S-Δ are at least as high as 20 g/L in DCE, mixing two equimolar solutions (5 g/L, 0.4 wt %) of R-Δ and S-Δ in DCE results, nonetheless, in the gelation of the mixture as evidenced by a homogeneous solid-like material that exhibits no gravitational flow whatsoever. Upon heating, the gel (0.4 wt %) transforms into a clear solution with a melting temperature of 69-73° C. which resorts on cooling to forming a gel, confirming its thermoreversibility. In addition, this gel has also been made by dissolving a racemate of solid R-Δ and S-Δ in DCE directly by heating, followed by cooling the mixture to ambient temperature. In contrast to the strong mirror-symmetrical circular dichroism (CD) responses of enantiopure R-Δ and S-Δ, the silent CD signal of a redissolved sample prepared from the centrifuged gel confirms (FIG. 1B) its racemic nature.

In view of the unexpected gelation of the racemate rac-Δ in DCE, the gelation abilities of rac-Δ in another five halogenated solvents were also assessed (Table 1). Enantiopure R-Δ and S-Δ are soluble in all of these solvents at the same concentration of 0.4 wt % under similar conditions. In striking contrast, upon mixing both equal volumes of 0.4 wt % solutions of R-Δ and S-Δ in these solvents, three different types of phenomena were observed—(i) self-supporting thermoreversible organogel which formed in DCE, (ii) white fibrous precipitates which appeared in CBE, CIE, and DBE within 10 min, and (iii) white flocculent precipitates which emerged after about 10 min in $CH_2Cl_2$ and $CHCl_3$. The morphologies of these different aggregated states of rac-Δ were probed by scanning electron microscopy (SEM).

TABLE 1

Solvent-Dependent Gelation Behavior of R-Δ and S-Δ as well as Their Racemate rac-Δ

| Solvent | R-Δ or S-Δ | rac-Δ |
|---|---|---|
| $CH_2Cl_2$ | S | P |
| $CHCl_3$ | S | P |
| $ClCH_2CH_2Cl$ | S | G |
| $ClCH_2CH_2Br$ | S | P |
| $ClCH_2CH_2I$ | S | P |
| $BrCH_2CH_2Br$ | S | P |

All experiments were carried out at the same concentration of 0.4 wt %. S, Solution; G, Gel; P, Precipitate.

Figure 2A:
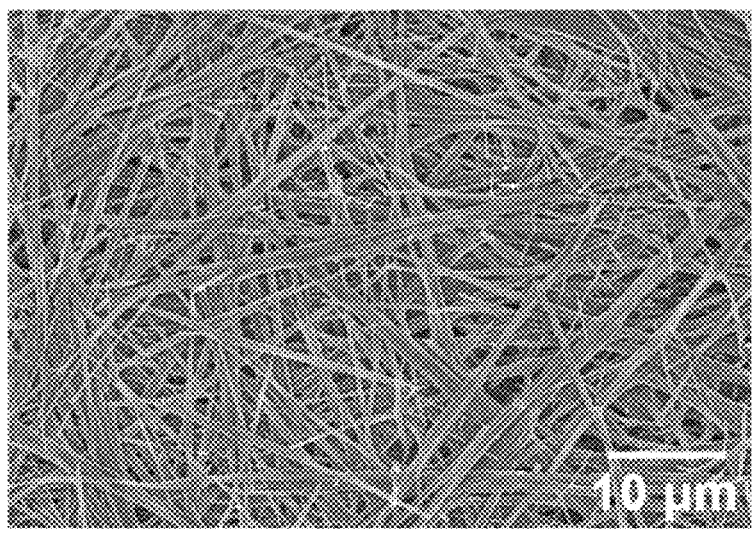
FIG. 2A shows interwoven fibrillar network from the gel of rac-Δ in $ClCH_2CH_2Cl$.
Figure 2B:
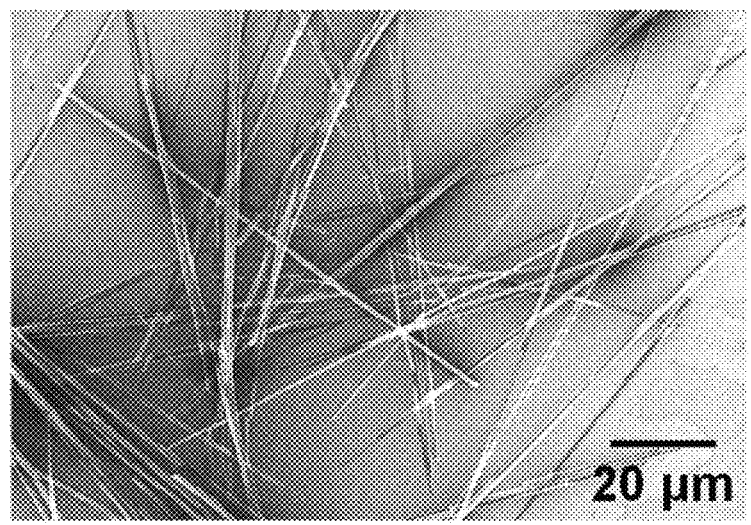
FIG. 2B shows discrete needles from a precipitate of rac-Δ in $BrCH_2CH_2Br$.
Figure 2C:
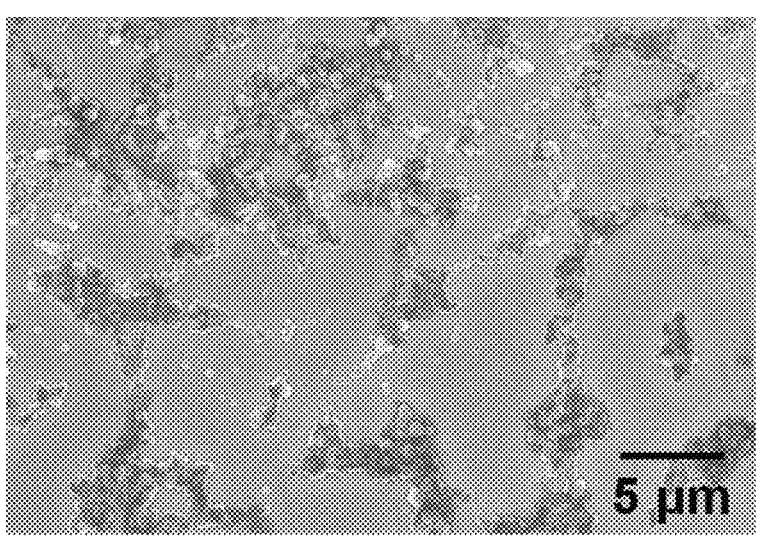
FIG. 2C shows random-shaped aggregates from a precipitate of rac-Δ in $CHCl_3$.
Figure 2D:
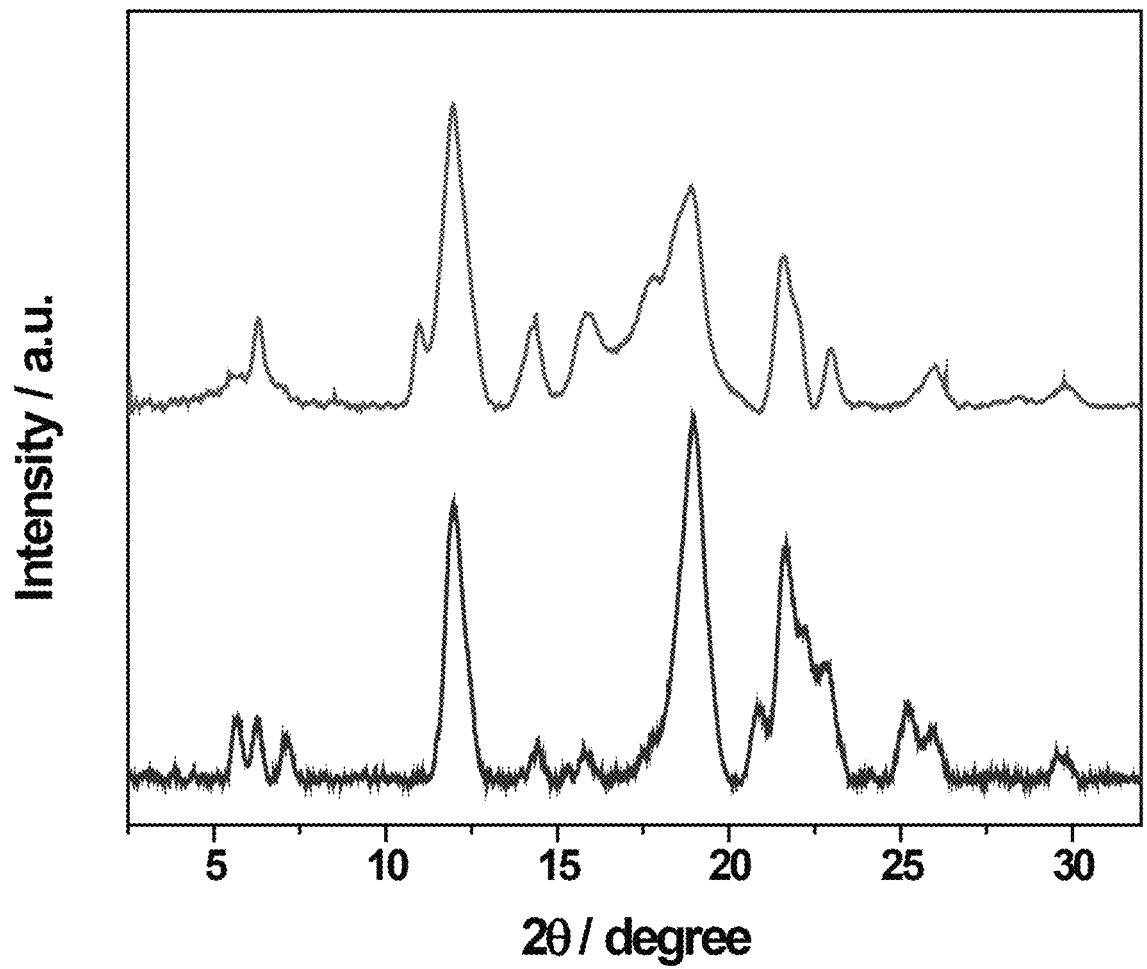
FIG. 2D shows powder X-ray diffraction patterns for the vacuum-evacuated gel of rac-Δ in $ClCH_2CH_2Cl$ (top) and the precipitate of rac-Δ in $BrCH_2CH_2Br$ (bottom).
Figure 3:
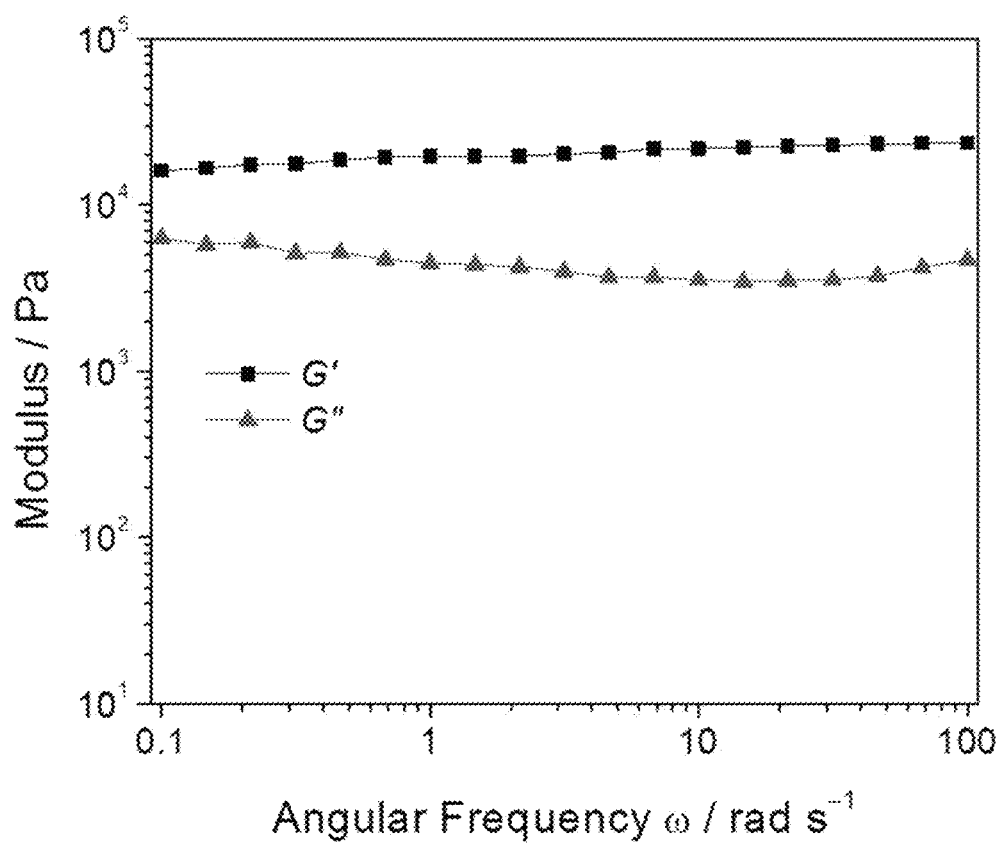
FIG. 3 shows a frequency sweep (0.02% strain) rheological measurements for the organogel of 1.0 wt % rac-Δ in $ClCH_2CH_2Cl$ at 25° C. G'=storage modulus; G"=loss modulus.

SEM Analysis of rac-Δ in DCE revealed (FIG. 2A) that the organogel is formed by an interwoven fibrillar network, composed of high-aspect ratio flexible fibers with lengths on the order of several hundred micrometers and diameters on the order of several hundred nanometers. The precipitate of rac-Δ in DBE has been characterized (FIG. 2B) as forming high-aspect ratio, but more rigid, as well as thicker and straight needles, which exercise their ability to generate an entangled network. This observation indicates that both the gel and the precipitate of rac-Δ in DCE and DBE, respectively, are generated by means of a similar mechanism involving the formation of high-aspect ratio 1D fibers as a result of cooperative action of the [X . . . X]-bonded DXE chains inside the NDI-Δ supramolecular nanotubes.[52] Good cooperation between the weaker [Cl . . . Cl] interactions and the shorter length of DCE (4.33 Å), compared with the stronger [Cl . . . Br], [Cl . . . I], and [Br . . . Br] interactions as well as the longer lengths exhibited in CBE (4.48 Å), CIE (4.68 Å), and DBE (4.62 Å), give rise to a more dense network of fibers which facilitates the gelation of rac-Δ in DCE involving the formation of the entangled fibrous network.[52] By contrast, SEM images of the flocks of rac-Δ in $CHCl_3$ show (FIG. 2C) random-shaped aggregates with variable diameters in size, suggesting that rac-Δ might be unable to aggregate unidirectionally, forming 1D fibers over a long range on account of the lack of the templating effect of the shorter constitution associated with $CHCl_3$.[52] The 1D fibers formed from rac-Δ in DCE and DBE were also investigated by powder X-ray diffraction (PXRD). Both PXRD patterns (FIG. 2D) for the vacuum-evacuated gel of rac-Δ in DCE and precipitate of rac-Δ in DBE resemble one another closely. The sharper diffraction peaks observed for the precipitate of rac-Δ in DBE are in line with the better rigidity and crystallinity of the 1D fibers formed from rac-Δ in DBE than that in DCE. These observations, in combination with our previous conclusion[52] that 1D supramolecular nanotubes form only from R-Δ or S-Δ in DXEs, (i) confirm the similar packing motifs of the 1D high-aspect ratio fibers, formed from rac-Δ in DCE and DBE and (ii) provide strong evidence for the same assembly mechanism of 1D fibers through columnar stacking of rac-Δ with the assistance of the templating effect of the [X . . . X]-bonded DXE chains.

Oscillatory rheology which was carried out in order to characterize the mechanical properties of the organogel (1.0 wt % rac-Δ in DCE), revealed (FIG. 2) that the storage modulus G' is 20 kPa which is greater than the corresponding loss modulus G" of 4 kPa. It is worth noting that the example of such a fully rigid macrocycle acting as a gelator at a concentration as low as 0.4 wt % without any additives except for the solvent is unprecedented to the best of our knowledge. In contrast, rac-Δ in CBE, CIE, and DBE produce more rigid high-aspect ratio fibers which are unable to form self-supporting gels through entangling to afford networks, leading to precipitation.

Atomic Force Microscopy (AFM) Analyses.

Figure 4A:
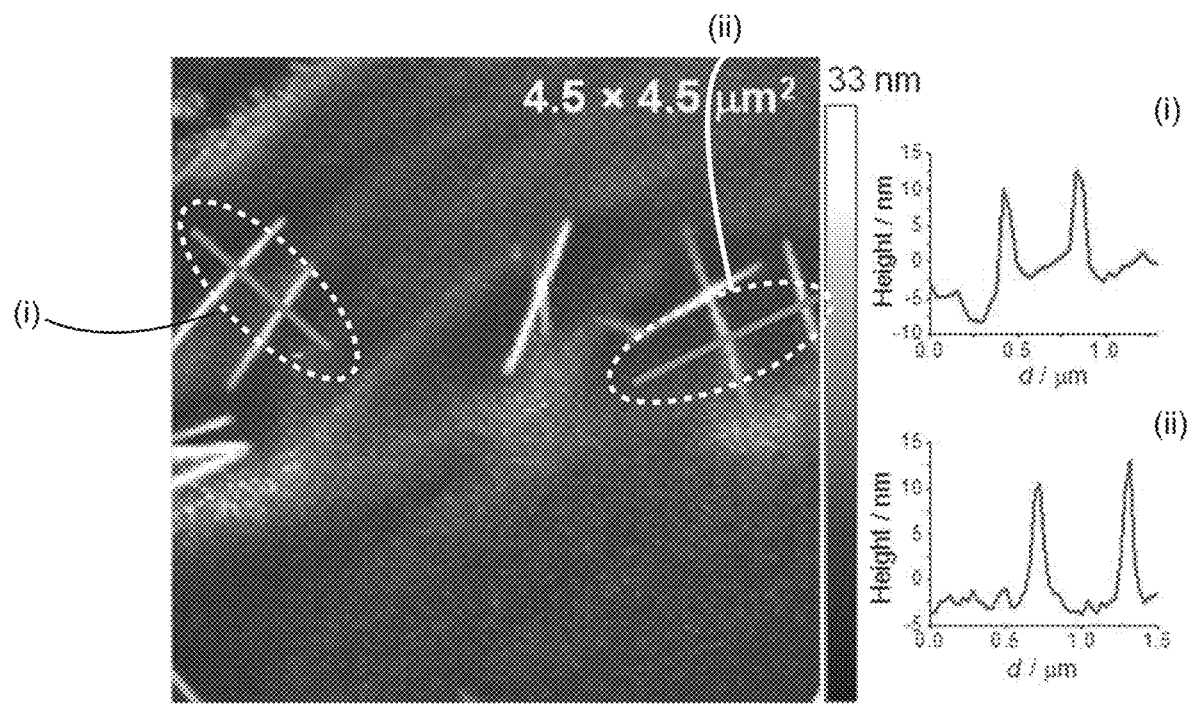
FIG. 4A shows height sensor images of a sample of rac-Δ in $ClCH_2CH_2Cl$ spin-coated on mica, in addition to the corresponding cross-sectional analysis of the nanofibers. The lines labelled (i) and (ii) in the height images correspond to the respective profile plots.
Figure 4B:
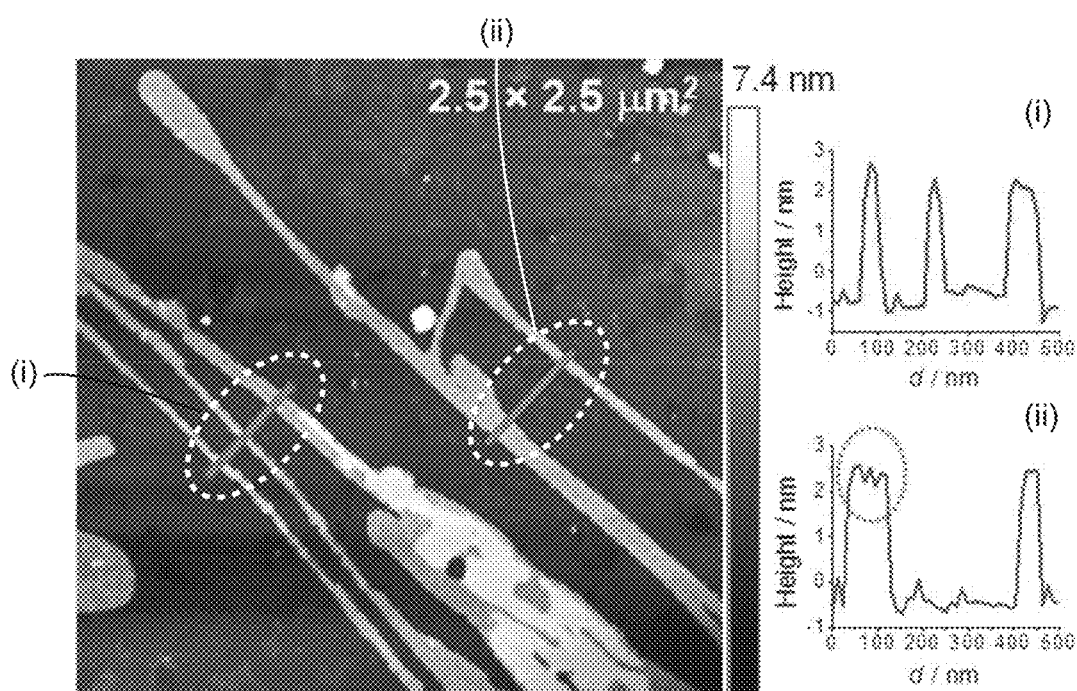
FIG. 4B shows height sensor images of a sample of rac-Δ in $BrCH_2CH_2Br$ spin-coated on mica, in addition to the corresponding cross-sectional analysis of the nanofibers. The lines labelled (i) and (ii) in the height images correspond to the respective profile plots. The circle in highlights the profile of parallel aggregated nanofibers.
Figure 4C:
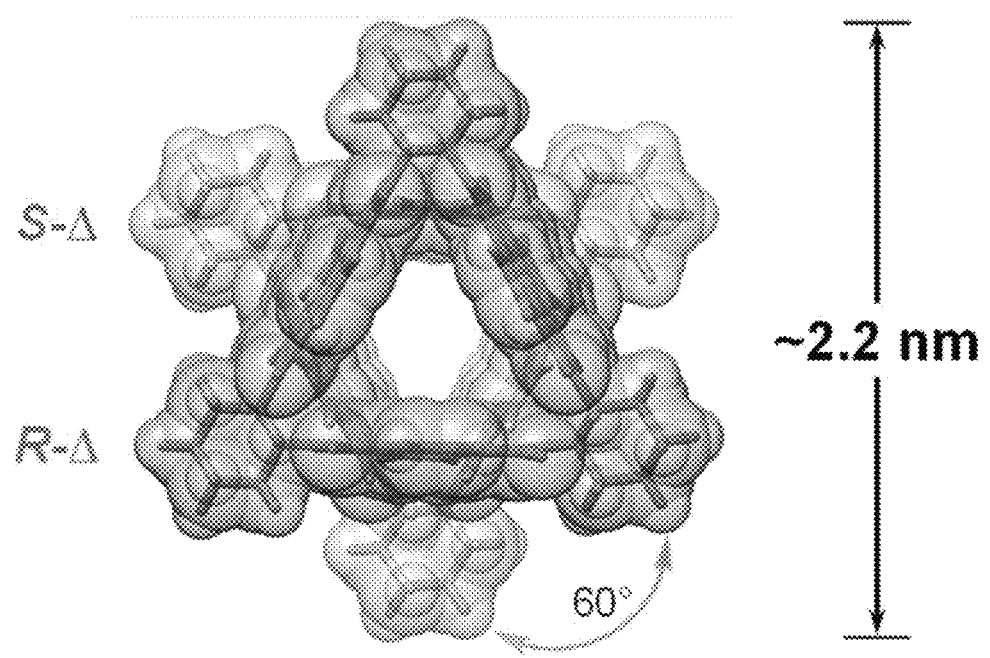
FIG. 4C shows a space-filling overlying a tubular representation of the top view of the columnar stacked dimer of R-Δ and S-Δ with a 60° rotational angle between them and an outer diameter of 2.2 nm.

In order to gain insight into the initial assembly mechanism of the high-aspect ratio fibers of rac-Δ in DCE and DBE, AFM was performed on them. Two samples were prepared by spin-coating both dilute clear solutions (0.5 g/L) of rac-Δ in DCE and DBE onto mica surfaces. The sample of rac-Δ in DCE reveals (FIG. 4A) discrete thin micrometer-long nanofibers with diameters of ca. 10 nm, which we believe are composed of a bundle of 2.2 nm-in-diameter supramolecular nanotubes formed (FIG. 4C) from the columnar stacking of alternate R-Δ and S-Δ with a 60° rotational angle. The AFM image of the sample of rac-Δ in DBE shows (FIG. 4B) high-aspect ratio nanotubes with lengths on the order of several micrometers. Cross-section analysis indicates unambiguously that these nanotubes have a height of 2.4±0.4 nm—a dimension which corresponds well with the outer diameter of 2.2 nm of the proposed R-Δ and S-Δ stacking in an alternating fashion to form (FIG. 4C) supramolecular nanotubes. This level of consistency confirms the fact that rac-Δ assembles into single supramolecular nanotubes with aspect ratios as high as 1000 or more as a result of the columnar stacking of rac-Δ in which R-Δ and S-Δ are positioned in a 60°-rotationally alternating manner. In addition, several single-molecule-scale nanotubes aggregate in parallel at long range, suggesting that the high-aspect ratio fibers observed in the SEM sample of rac-A in DBE could be assembled from a bundle of supramolecular nanotubes with diameters of 2.2 nm. Considering the closely similar PXRD patterns (FIG. 2D) of the gel of rac-Δ in DCE and the precipitate of rac-Δ in DBE, the formation of thicker nanofibers in the case of rac-Δ in DCE compares with that in DBE. The nanofibers are believed to originate from the parallel packing of single-molecule-scale supramolecular nanotubes as a consequence of the rapid volatilization of low-boiling DCE during the spin-coating process. The observation of high-aspect ratio supramolecular nanotubes with diameters on the single-molecule scale also indicates that the axial noncovalent bonding interactions—namely, [C—H . . . O] and [X . . . X] between DXE molecules inside the nanotubes—play a defining role in directing and driving the highly efficient formation of these 1D assemblies.

Density Functional Theory (DFT) Calculations.

Figures 5A, 5B:
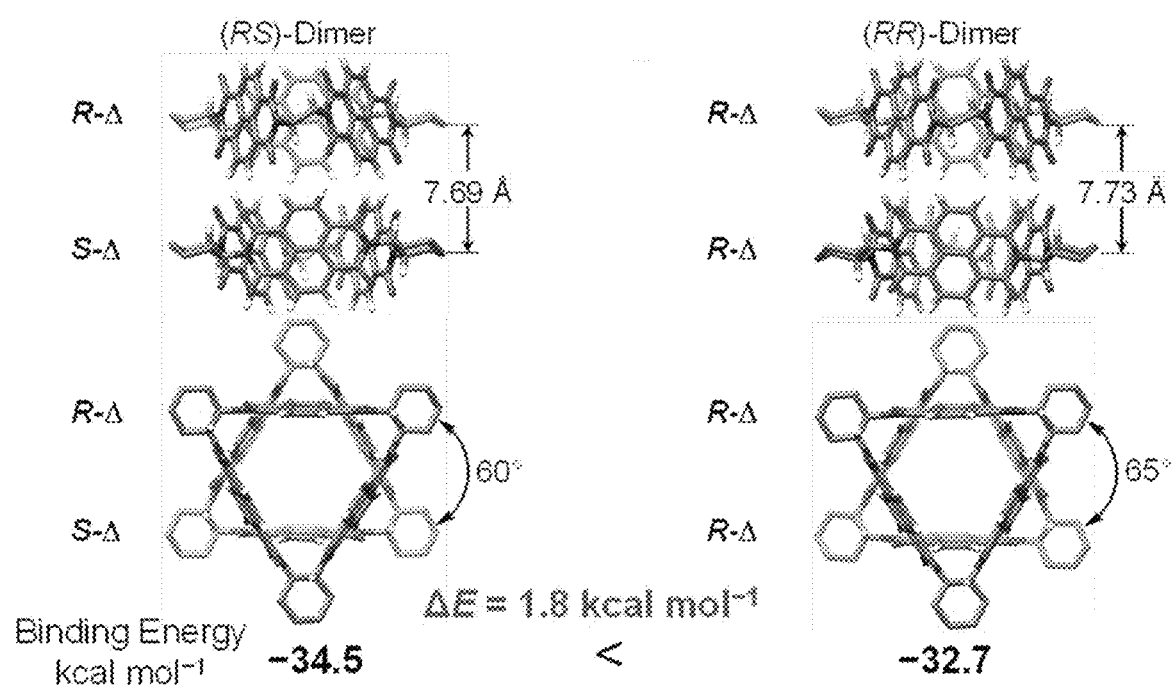
FIG. 5A presents results of DFT calculations for a side-on and top view of stick models showing the relative orientations of R-Δ and S-Δ in the optimized superstructures of the (RS)-dimer.
FIG. 5B presents results of DFT calculations for a side-on and top view of stick models showing the relative orientations of R-Δ and S-Δ in the optimized superstructures of the (RR)-dimer (b). Hydrogen atoms on achiral carbon atoms of 1,2-cyclohexano rings are omitted for the sake of clarity.
Figure 5C:
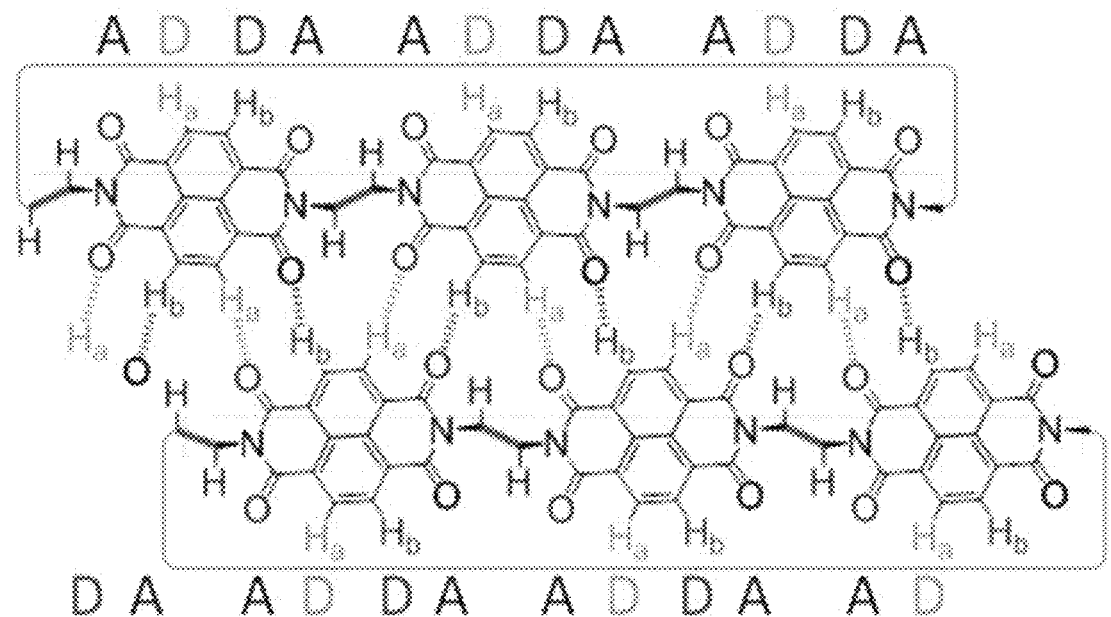
FIG. 5C shows schematic views of the [C—H . . . O] interactions (hatched lines) between two NDI-Δ macrocycles of the (RS)-dimer, as well as the relative positions of the diastereotopic NDI protons $H_a$ (cis,) and $H_b$ (trans) to the adjacent protons on the stereogenic center of the 1,2-cyclohexano rings. $[C_a—H_a . . . O]$ and $[C_b—H_b . . . O]$ hydrogen bonds are depicted as hatched lines. A and D indicate hydrogen bonding acceptors and donors, respectively.
Figure 5D:
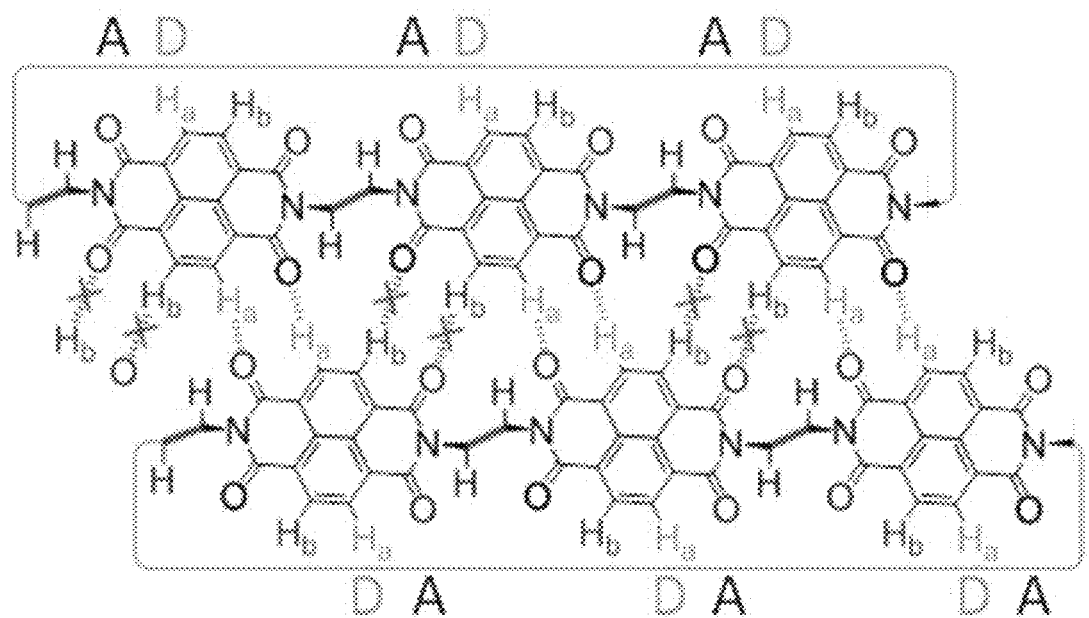
FIG. 5D shows schematic views of the [C—H . . . O] interactions (hatched lines) between two NDI-Δ macrocycles of the (RR)-dimer, as well as the relative positions of the diastereotopic NDI protons $H_a$ (cis,) and $H_b$ (trans) to the adjacent protons on the stereogenic center of the 1,2-cyclohexano rings. $[C_a—H_a ... O]$ and $[C_b—H_b ... O]$ hydrogen bonds are depicted as hatched lines. A and D indicate hydrogen bonding acceptors and donors, respectively. Crosses indicate non-existent [C—H ... O] hydrogen bonds on account that $d_{C ... O}$>3.5 Å.
Figure 5E:
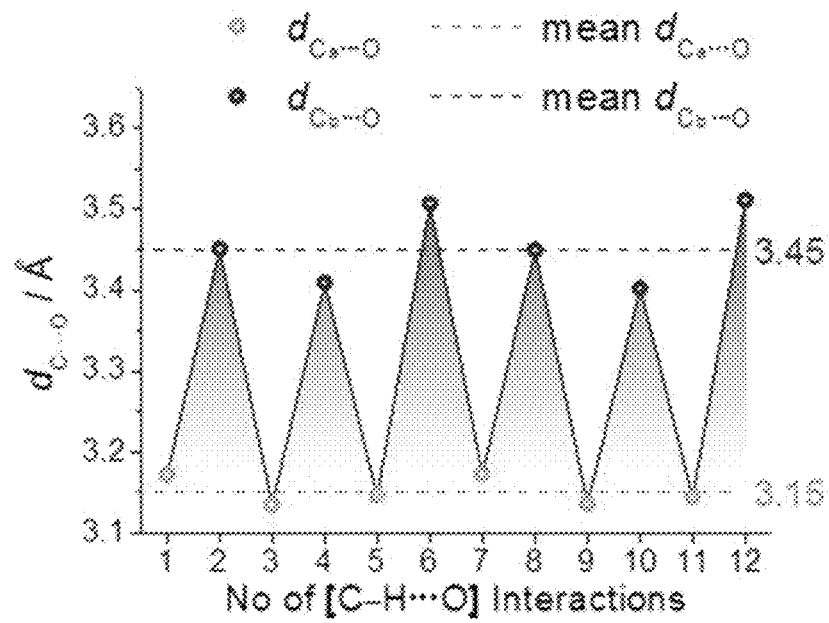
FIG. 5E shows an analysis of $d_{C ... O}$ of [C—H ... O] interactions between two NDI-Δ macrocycles of the (RS)-dimer.
Figure 5F:
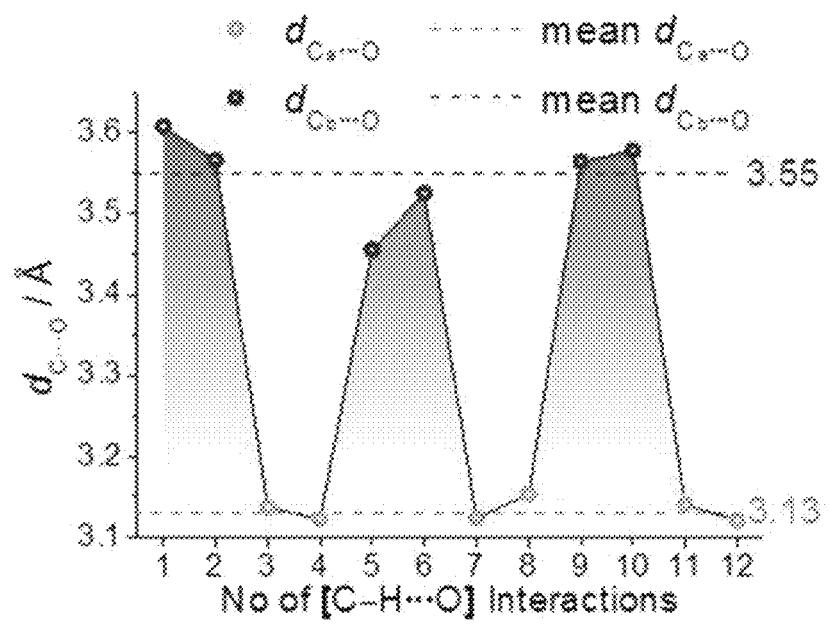
FIG. 5F shows an analysis of $d_{C ... O}$ of [C—H ... O] interactions between two NDI-Δ macrocycles of the (RR)-dimer.

In an attempt to understand why the racemate rac-Δ forms gels and precipitates while the pure enantiomers R-Δ and S-Δ do not, we investigated these systems by quantum chemical calculations (Q-Chem 4.2.0/PBE/6-311G**). We do not intend to be bound by theory, but believe that these numerical experiments are useful for those of skill in the art to more fully understand the present technology. As models, we studied two representative systems—that is, a racemic (RS)-dimer and an enantiopure (RR)-dimer composed (FIGS. 5A and 5B) of columnarly stacked R-Δ and S-Δ or two R-Δs, respectively. DFT optimization results revealed that the (RS)-dimer has a binding energy (ΔG) of −34.5 kcal mol$^{-1}$, whereas the (RR)-dimer has a ΔG value of −32.7 kcal mol$^{-1}$. It follows that the (RS)-dimer is 1.8 kcal mol$^{-1}$ more stable than the (RR)-dimer on the basis of the same energies considered for R-Δ and S-Δ, an observation which suggests that the aggregates of rac-Δ should be thermodynamically more stable than those of the either R-Δ or S-Δ, and thus is in good agreement with the experimental results observed (FIG. 2) for the formation of the aggregates of rac-Δ while R-Δ remains in solution. The binding energy difference of 1.8 kcal mol$^{-1}$ equates well with the modest melting temperature (69-73° C.) of the gel. Geometrical analysis revealed (FIGS. 5A and 5B) that (i) the two NDI-Δs in the (RS)-dimer are 0.04 Å closer than in the (RR)-dimer, and (ii) the rotational angle between two NDI-Δs in the (RS)-dimer is 60°, giving rise to the $C_3$ symmetry of the (RS)-dimer, whereas the angle in the (RR)-dimer is 65° with a 5° deviation from $C_3$ symmetry. These observations suggest two possibilities—(i) the [C—H . . . O] hydrogen bonding interactions between R-Δ and S-Δ are stronger than those between two R-Δs; and (ii) the columnar stacking of the (RS)-dimer leads to non-helical supramolecular nanotubes, while that of the (RR)-dimer results in helical ones as shown previously.[52] The [C—H . . . O] hydrogen bonding patterns of both dimers are depicted in FIGS. 5C and 5D wherein the diastereotopic NDI protons are designated as $H_a$ and $H_b$, the corresponding C atoms of which are referred as $C_a$ and $C_b$. Analysis of [C—H . . . O] interaction distances $d_{C\ldots O}$ reveals (FIGS. 5E and 5F, Table 3) that in both dimers, all $d_{Cb\ldots O}$ are much greater than all $d_{Ca\ldots O}$. All $d_{Ca\ldots O}$ in both dimers are very close with a mean $d_{Ca\ldots O}$ of 3.15 Å (mean $\angle C_a$—$H_a$ . . . O of 152.1°) for the (RS)-dimer and one of 3.13 Å (mean $\angle C_a$—$H_a$ . . . O of) 161° for the (RR)-dimer, respectively, suggesting that all the $H_a$ atoms form strong [$C_a$—$H_a$ . . . O] hydrogen bonds with imide O atoms. By contrast, mean $d_{Cb\ldots O}$ of 3.45 Å (mean $\angle C_b$—$H_b$ . . . O of 161.8°) in the (RS)-dimer is 0.1 Å, shorter than the one of 3.55 Å (mean $\angle C_b$—$H_b$ . . . O of 152.3°) in the (RR)-dimer—an all but negligible value to be considered as a [C—H . . . O] interaction, [53] indicating that there are modest [$C_b$—$H_b$ . . . O] interactions in the (RS)-dimer, whereas [$C_b$—$H_b$ . . . O] interactions in the (RR)-dimer are nonexistent. In the case of the (RS)-dimer, [$C_a$—$H_a$ . . . O] and [$C_b$—$H_b$ . . . O] hydrogen bonds are alternatingly arranged (FIG. 5E) in a triangular wave with an unprecedented and uninterrupted complementary 12-point ADDAADDAADDA•DAADDAADDAAD hydrogen-bonding sequence. While in the case of the (RR)-dimer, [$C_a$—$H_a$ . . . O] and [$C_b$—$H_b$ . . . O] hydrogen bonds are doubly alternatingly arranged (FIG. 5F) in a square-wave manner with a complementary six-point ADADAD•DADADA hydrogen bonding sequence on account of the weakness of the [$C_b$—$H_b$ . . . O] hydrogen bonds. The stronger [$C_b$—$H_b$ . . . O] hydrogen bonds—which are in good agreement with the shorter distance between two NDI-Δs and lower energy of the (RS)-dimer—in cooperation with the more even arrangement of alternating strong and weak hydrogen bonds, endow rac-Δ with a stronger ability to aggregate giving fibers, whereas neither R-Δ nor S-Δ can form similar aggregates under the same conditions on account of the less stable noncovalent bonding interactions, resulting from the inferior stereochemical match between of two R-Δs or S-Δs. These observations, taken together, suggest that the energetically more favorable match between R-Δ and S-Δ allows them to act as two unique double-faced 12-point [C—H . . . O] hydrogen-bonded rings which are able to enhance the cooperativity and directionality of the hydrogen bonds, resulting in the 1D supramolecular assembly of rac-Δ. [54, 55] Although strong [O—H . . . O], [44, 45] [N—H . . . O], [29, 30, 41, 46-49] π-π stacking, [47, 56-59] and ion-pairing[60, 61] interactions, as well as weak halogen bonding[62] and [C—H . . . π][63] interactions have been employed oftentimes in supramolecular polymerizations, related examples facilitated predominantly by multiple weak [C—H . . . O] interactions[64, 65] acting circularly and cooperatively have not, to the best of our knowledge, been explored.

$^1$H and 2D DOSY NMR Analyses.

Figure 6A:
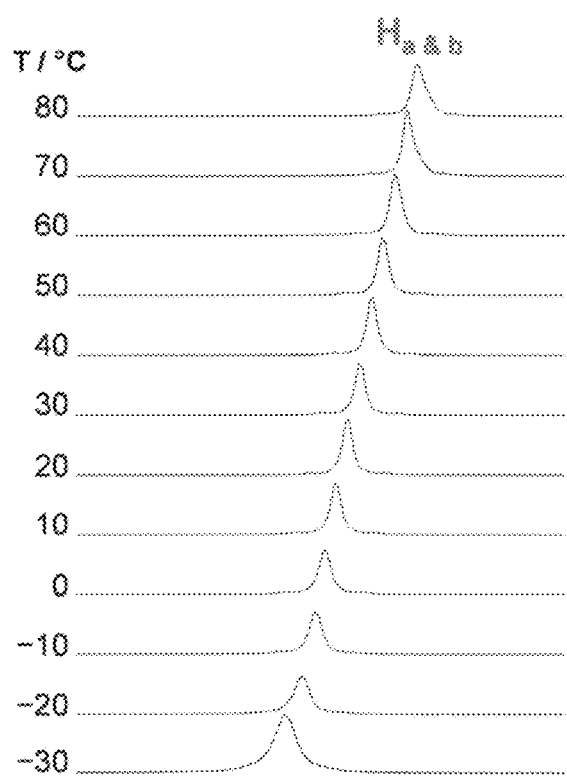
FIG. 6A shows variable temperature $^1$H NMR analyses of rac-Δ in ClCD$_2$CD$_2$Cl. Partial $^1$H NMR spectra of rac-Δ recorded at the same concentration of 0.6 g/L from −30 to +80° C. The relative positions of the diastereotopic NDI protons $H_a$ and $H_b$ to the adjacent protons on the stereogenic center of the 1,2-cyclohexano moieties are assigned in FIGS. 5C and 5D.
Figure 6B:
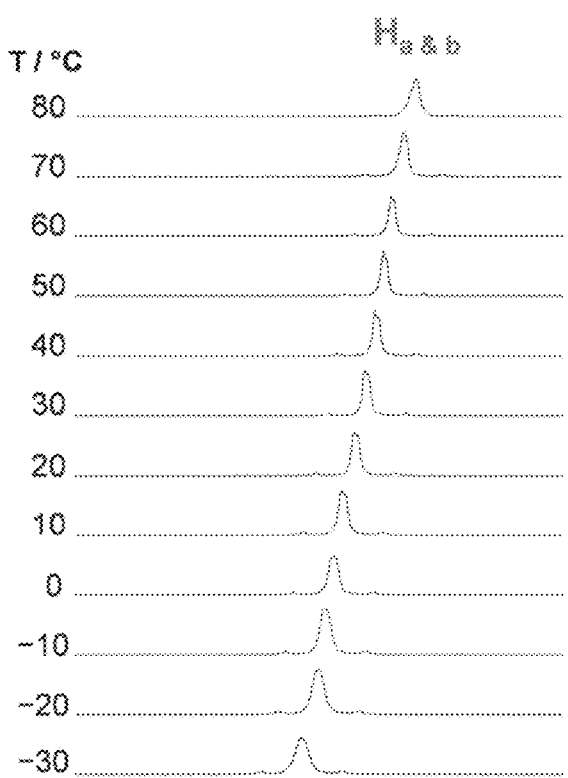
FIG. 6B shows variable temperature $^1$H NMR analyses of R-Δ in ClCD$_2$CD$_2$Cl. Partial $^1$H NMR spectra of R-recorded at the same concentration of 0.6 g/L from −30 to +80° C. The relative positions of the diastereotopic NDI protons $H_a$ and $H_b$ to the adjacent protons on the stereogenic center of the 1,2-cyclohexano moieties are assigned in FIGS. 5C and 5D.
Figure 7A:
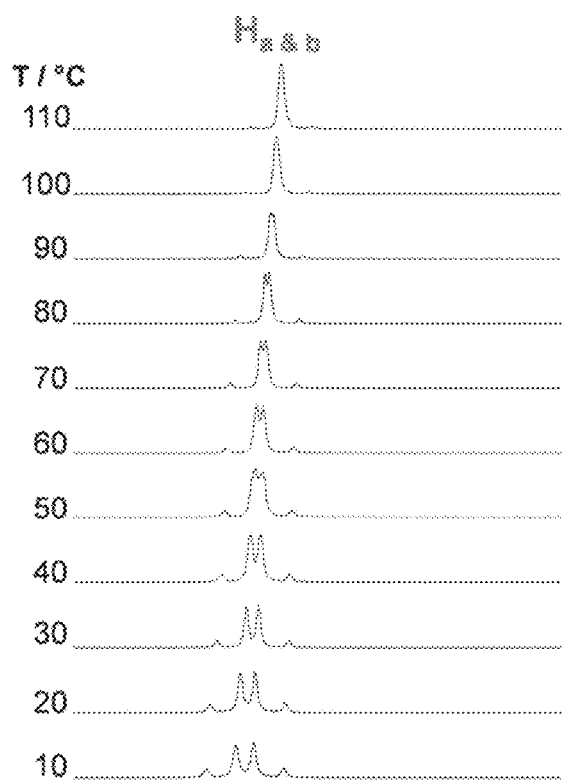
FIG. 7A shows variable temperature $^1$H NMR analyses of rac-Δ in BrCD$_2$CD$_2$Br. Partial $^1$H NMR spectra of rac-Δ recorded at the same concentration of 0.6 g/L from +10 to +110° C. The relative positions of the diastereotopic NDI protons $H_a$ and $H_b$ to the adjacent protons on the stereogenic center of the 1,2-cyclohexano moieties are assigned in FIGS. 5C and 5D.
Figure 7B:
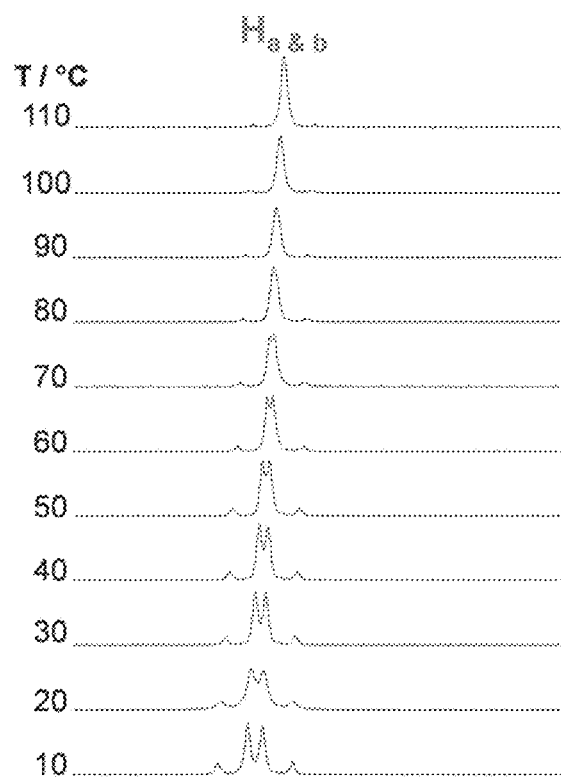
FIG. 7B shows variable temperature $^1$H NMR analyses of R-Δ in BrCD$_2$CD$_2$Br. Partial $^1$H NMR spectra of R-Δ recorded at the same concentration of 0.6 g/L from +10 to +110° C. The relative positions of the diastereotopic NDI protons $H_a$ and $H_b$ to the adjacent protons on the stereogenic center of the 1,2-cyclohexano moieties are assigned in FIGS. 5C and 5D.
Figure 8A:
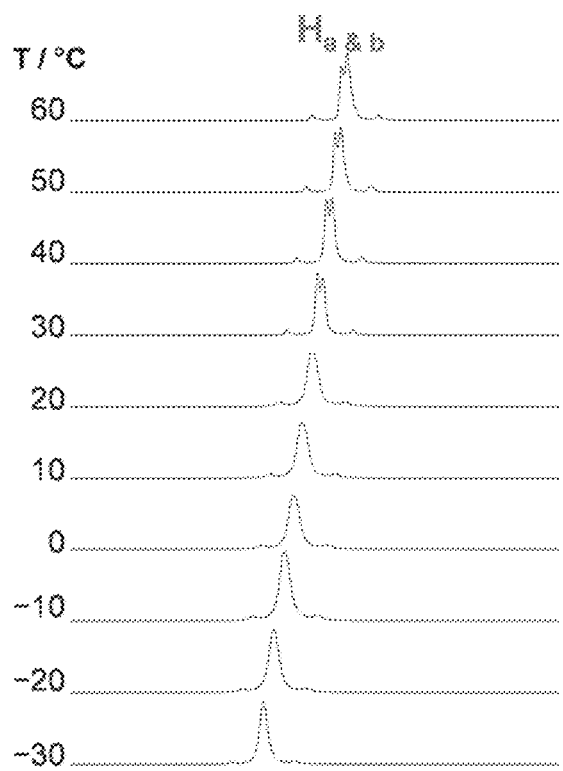
FIG. 8A shows variable temperature $^1$H NMR analyses of rac-Δ in CDCl$_3$. Partial $^1$H NMR spectra of rac-Δ recorded at the same concentration of 0.6 g/L from −30 to +60° C. The relative positions of the diastereotopic NDI protons $H_a$ and $H_b$ to the adjacent protons on the stereogenic center of the 1,2-cyclohexano moieties are assigned in FIGS. 5C and 5D.
Figure 8B:
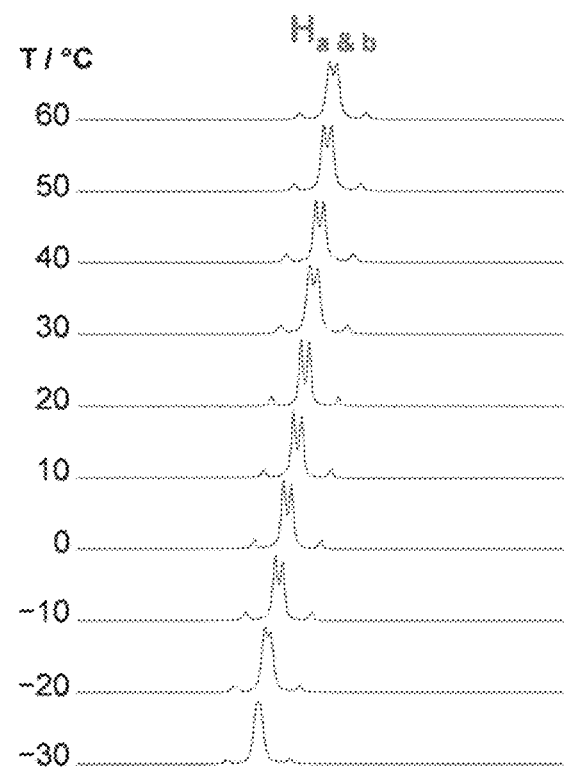
FIG. 8B shows variable temperature $^1$H NMR analyses of R-Δ in CDCl$_3$. Partial $^1$H NMR spectra of R-Δ recorded at the same concentration of 0.6 g/L from −30 to +60° C. The relative positions of the diastereotopic NDI protons $H_a$ and $H_b$ to the adjacent protons on the stereogenic center of the 1,2-cyclohexano moieties are assigned in FIGS. 5C and 5D.

In order to probe the possible influence of different strengths of [C—H . . . O] interactions between R-Δ and S-Δ as well as enantiopure R-Δ on the chemical shifts of the diastereotopic NDI protons $H_a$ and $H_b$, variable-temperature (VT) $^1$H NMR spectroscopy was carried out. All VT $^1$H NMR spectra of rac-Δ and R-Δ carried out in ClCD$_2$CD$_2$Cl (−30 to +80° C., FIGS. 6A and 6B), BrCD$_2$CD$_2$Br (+10 to +110° C., FIGS. 7A and 7B), and CDCl$_3$ (−30 to +60° C., FIGS. 8A and 8B) at the same concentration show similar trends with no significant differences between the changes in chemical shifts of $H_a$ and $H_b$ of both rac-Δ and R-Δ, an observation which indicates that the weak nature of [C—H . . . O] interactions might not be enough to lead to the $^1$H NMR-detectable difference of chemical environments between rac-Δ and R-Δ, even if the [C—H . . . O] interactions between R-Δ and S-Δ are stronger than those between two R-Δs as supported by DFT calculations. DOSY NMR experiments were performed to investigate the aggregation behaviors of rac-Δ and R-Δ in the solution phase. DOSY NMR spectra of both rac-Δ and R-Δ in ClCD$_2$CD$_2$Cl, BrCD$_2$CD$_2$Br, and CDCl$_3$, analyzed under the same conditions, gave very similar diffusion coefficients (D) (Table 2). For example, although flocks already appeared in solutions of rac-Δ, those of R-Δ are still clear at −30° C. with the concentration of 0.6 g/L in ClCD$_2$CD$_2$Cl, D of rac-Δ and R-Δ are measured to be 0.82×10$^{-10}$ and 0.84×10$^{-10}$ m$^2$ s$^{-1}$, respectively. These observations suggest that the gelation and precipitation of rac-Δ, rather than enantiopure R-Δ or S-Δ, might be the result of a cooperative mechanism facilitated by the subtle interplay between [C—H . . . O] interactions and better matched steric configurations of R-Δ and S-Δ, which is not detectable on the $^1$H NMR timescale by DOSY experiments presumably because of the rapid dynamic exchange of species in solution phase.

TABLE 2

DOSY NMR determined diffusion coefficients (D) for R-Δ and rac-Δ in different solvents and at different temperatures

|  | R-Δ | rac-Δ | R-Δ | rac-Δ | R-Δ | rac-Δ |
|---|---|---|---|---|---|---|
| Solvent | CDCl$_3$ | | | | | |
| Temp. (° C.) | −30 | −30 | 10 | 10 | 80 | 80 |
| D (10$^{-10}$ m$^2$ s$^{-1}$) | 0.84 | 0.82 | 2.14 | 2.18 | 6.52 | 6.60 |
| Solvent | BrCD$_2$CD$_2$Br | | | | | |
| Temp. (° C.) | 10 | 10 | 20 | 20 | 80 | 80 |
| D (10$^{-10}$ m$^2$ s$^{-1}$) | 1.05 | 1.03 | 1.25 | 1.24 | 3.25 | 3.25 |
| Solvent | CDCl$_3$ | | | | | |
| Temp. (° C.) | −30 | −30 | 20 | 20 | | |
| D (10$^{-10}$ m$^2$ s$^{-1}$) | 2.12 | 2.12 | 7.14 | 7.14 | | |

In summary, we have demonstrated that equimolar mixing of R-Δ and S-Δ leads to the assembly of the racemate rac-Δ into a supramolecular organogel composed of entangled fibrillar networks in DCE, whereas neither of the enantiopure R-Δ nor S-Δ form fibrous aggregates under identical conditions. These organogels are comprised of fibers, produced by the columnar stacking of alternate R-Δ and S-Δ and driven synergistically by rings of 12 weak [C—H . . . O] hydrogen bonds in a circular manner, assisted by a good match between the R-Δ and S-Δ enantiomers. DFT calculations testify to the fact that the (RS)-dimer is 1.8 kcal mol$^{-1}$ more stable than the (RR)-dimer and that the [C—H . . . O] interactions between R-Δ and S-Δ are much stronger and more highly cooperative than those between two R-Δs or S-Δs. These experimental results, in conjunction with DFT calculations, provide and account for this example of supramolecular gelation from rigid racemic gelators, rather than their enantiopure counterparts, an observation which highlights the fundamental relationship between stereochemistry and gelation. The use of the multiple weak [C—H . . . O] interactions acting cooperatively in rings to provide the major driving force represents a promising design strategy for LMWGs which relies on the subtle interplay between stereochemistry and weak noncovalent bonding interactions, expanding the scope of LMWGs to rigid racemates in the absence of strong hydrogen-bonded motifs and flexible structures. In view of the fact that many organic compounds contain (C—)H atoms and C═O groups (or O atoms) that can play the roles of hydrogen bond donors and acceptors, respectively, means that intramolecular arrays with intermolecular stereoelectronic matches of multiple [C—H . . . O] interactions can, in principle, act cooperatively in a supramolecular context to produce a wide variety of new soft materials.

Miscellaneous

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

General

All reagents were purchased from Aldrich or TCI and used without further purification. The macrocyclic triangles R-Δ (Formula I) and S-Δ (Formula II) were synthesized as described previously.[51] Variable temperature $^1$H and 2D DOSY NMR spectra were recorded on a BrukerAvance 500 spectrometer, with a working frequency of 500 MHz for $^1$H. Chemical shifts are reported in ppm relative to the signals corresponding to the residual non-deuterated solvents (CDCl$_3$: δ 7.26 ppm; ClCD$_2$CD$_2$Cl: δ 3.72 ppm; BrCD$_2$CD$_2$Br: δ 3.63 ppm). Circular dichroism (CD) measurements were carried out on a Jasco J-815 spectrometer and the HT voltage was maintained below 600 V.

Preparation and Characterization of Organogels and Precipitates

Gel and precipitate formations were carried out by mixing equal volumes of solutions of both R-Δ and S-Δ in vials at the same concentrations of 0.4 wt %. The gels can also be made by directly dissolving the racemate rac-Δ as a solid in ClCH$_2$CH$_2$Cl (DCE) by heating, followed by cooling the mixture to ambient temperature. The melting point of the gel (0.4 wt %) was measured using an electrothermal IA9100 melting point apparatus. The scanning electron microscopy (SEM) samples were prepared by drop-casting as-synthesized aggregates onto silicon wafers, followed by drying in air. SEM Images were obtained using a Hitachi SU-8030 FE-SEM. Powder X-ray diffraction (PXRD) data were collected on a Rigaku ATXG X-ray diffractometer using Cu-K$_\alpha$ radiation (λ=1.54178 Å, 50 kV, 240 mA) at room temperature.

Rheological measurements were performed on a Paar Physica MCR-300 rheometer using a 25 mm diameter parallel plate with a 1.0 mm gap. The organogel samples were prepared by dissolving the racemate rac-Δ (1.0 wt %) directly as a solid in DCE by heating, followed by cooling the mixture to ambient temperature. Gel samples were loaded carefully onto the bottom plate. Frequency sweep experiments were conducted within the linear viscoelastic regime.

In order to obtain aggregates as small as possible for atomic force microscopy (AFM) characterization, the as-synthesized gel and precipitate (5 mg of rac-Δ in 1 mL of DCE or DBE) was diluted to a concentration of 0.5 g/L and spin-coated onto a mica surface at 5000 rpm and dried in air. AFM Imaging was performed immediately on a Dimension ICON, Bruker Corporation using the tapping mode. The cross sections and heights of individual fibers were analyzed employing built-in software.

Computational Details

Density functional theory (DFT) calculations for both model dimers and both R-Δ and S-Δ were carried out using Q-Chem,[2] version number 4.2.0.[68] The Perdew-Burke-Ernzerhof[3] (PBE) type of GGA exchange-correlation functional was applied for geometry optimizations with the 6-311G** basis set.[69] The van der Waals correction was taken into account using Grimme's empirical dispersion potential.[70] The geometries of individual R-Δ and S-Δ as well as both (RR)- and (RS)-dimers were optimized in the gas phase. The binding energies for holding (i) R-Δ and S-Δ molecules together to form the (RS)-dimer or (ii) two R-Δ molecules to form the (RR)-dimer were calculated (FIG. S3) using the energy differences between both (RR)-dimer and (RS)-dimer with their corresponding isolated monomeric triangles. The optimized coordinates of R-Δ and S-Δ as well as those for the (RS)- and (RR)-dimers are provided in Tables 4-7. Structural images of individual R-Δ and S-Δ as well as both (RR)- and (RS)-dimers were produced using UCSF Chimera 1.10. Atom-to-atom distances and angles were measured (Table 3) employing Mercury 3.6.

TABLE 3

[C—H . . . O] Hydrogen Bonding Geometries of DFT Optimized Structures of the (RS)- and (RR)-Dimers.

| Dimer | No[a] | [C—H . . . O] Interaction[a] | $d_{C—H}$/Å | $d_{H...O}$/Å | $d_{C...O}$/Å | ∠C—H . . . O/° |
|---|---|---|---|---|---|---|
| (RS)-dimer | 1 | [C$_a$—H$_a$ . . . O] | 1.092 | 2.1758 | 3.1719 | 150.47 |
| | 2 | [C$_b$—H$_b$ . . . O] | 1.0937 | 2.3858 | 3.4518 | 164.4 |
| | 3 | [C$_a$—H$_a$ . . . O] | 1.0925 | 2.1312 | 3.135 | 151.51 |
| | 4 | [C$_b$—H$_b$ . . . O] | 1.0934 | 2.3634 | 3.4096 | 159.58 |
| | 5 | [C$_a$—H$_a$ . . . O] | 1.0925 | 2.1268 | 3.1468 | 154.25 |
| | 6 | [C$_b$—H$_b$ . . . O] | 1.0936 | 2.453 | 3.5073 | 161.5 |
| | 7 | [C$_a$—H$_a$ . . . O] | 1.092 | 2.176 | 3.1728 | 150.57 |
| | 8 | [C$_b$—H$_b$ . . . O] | 1.0937 | 2.3839 | 3.4504 | 164.56 |
| | 9 | [C$_a$—H$_a$ . . . O] | 1.0925 | 2.1309 | 3.1363 | 151.75 |
| | 10 | [C$_b$—H$_b$ . . . O] | 1.0934 | 2.3573 | 3.4027 | 159.45 |
| | 11 | [C$_a$—H$_a$ . . . O] | 1.0924 | 2.1268 | 3.1449 | 153.93 |
| | 12 | [C$_b$—H$_b$ . . . O] | 1.0936 | 2.4588 | 3.5118 | 161.2 |
| (RR)-dimer | 1 | [C$_b$—H$_b$ . . . O] | 1.0931 | 2.6062 | 3.6084 | 152.05 |
| | 2 | [C$_b$—H$_b$ . . . O] | 1.0932 | 2.5655 | 3.5668 | 151.84 |
| | 3 | [C$_a$—H$_a$ . . . O] | 1.093 | 2.0775 | 3.1371 | 162.5 |
| | 4 | [C$_a$—H$_a$ . . . O] | 1.0928 | 2.0662 | 3.1228 | 161.73 |
| | 5 | [C$_b$—H$_b$ . . . O] | 1.0932 | 2.4512 | 3.4561 | 152.21 |
| | 6 | [C$_b$—H$_b$ . . . O] | 1.0935 | 2.5111 | 3.5261 | 153.89 |
| | 7 | [C$_a$—H$_a$ . . . O] | 1.0926 | 2.0761 | 3.1239 | 159.68 |
| | 8 | [C$_a$—H$_a$ . . . O] | 1.093 | 2.0933 | 3.1535 | 162.65 |
| | 9 | [C$_b$—H$_b$ . . . O] | 1.0933 | 2.5605 | 3.565 | 152.31 |
| | 10 | [C$_b$—H$_b$ . . . O] | 1.0931 | 2.5805 | 3.5784 | 151.35 |
| | 11 | [C$_a$—H$_a$ . . . O] | 1.0926 | 2.0971 | 3.1404 | 158.72 |
| | 12 | [C$_a$—H$_a$ . . . O] | 1.0928 | 2.0681 | 3.1212 | 160.88 |

[a]The numbers (No) and types of [C—H . . . O] interactions have been assigned in FIGS. 4c-f in the main text.

TABLE 4

Optimized Coordinates of R-Δ Using PBE/6-311G**.

| Atom Number | Atom Symbol | x/Å | y/Å | z/Å |
|---|---|---|---|---|
| 1 | O | 5.39053 | 0.97407 | −1.99443 |
| 2 | O | −0.30164 | 5.09809 | −2.58105 |
| 3 | O | −0.59292 | 5.32502 | 2.00668 |
| 4 | O | 4.89396 | 0.93472 | 2.586 |
| 5 | O | −3.41264 | 4.10317 | −2.05773 |
| 6 | O | −4.39116 | −2.86729 | −2.51364 |
| 7 | O | −4.27162 | −3.18747 | 2.07517 |
| 8 | O | −3.28059 | 3.77932 | 2.5385 |
| 9 | O | −1.92972 | −4.90524 | −2.01996 |
| 10 | O | 4.5123 | −2.09152 | −2.57218 |
| 11 | O | 4.94954 | −2.22093 | 2.01234 |
| 12 | O | −1.57772 | −4.82146 | 2.57359 |
| 13 | N | 5.0774 | 0.81774 | 0.28439 |
| 14 | N | −0.57638 | 5.08646 | −0.28639 |
| 15 | N | −3.2094 | 3.95536 | 0.2341 |
| 16 | N | −4.16492 | −3.07519 | −0.22276 |
| 17 | N | −1.83874 | −4.74231 | 0.27758 |
| 18 | N | 4.7029 | −2.00725 | −0.27004 |
| 19 | C | 4.72954 | 1.27446 | −1.0052 |
| 20 | C | 3.5177 | 2.13219 | −1.1094 |

TABLE 4-continued

Optimized Coordinates of R-Δ Using PBE/6-311G**.

| Atom Number | Atom Symbol | x/Å | y/Å | z/Å |
|---|---|---|---|---|
| 21 | C | 3.07008 | 2.54291 | −2.36249 |
| 22 | H | 3.62005 | 2.20363 | −3.24262 |
| 23 | C | 1.94009 | 3.37533 | −2.47922 |
| 24 | H | 1.57572 | 3.7036 | −3.45477 |
| 25 | C | 1.26234 | 3.81041 | −1.34274 |
| 26 | C | 0.08202 | 4.70462 | −1.48633 |
| 27 | C | −0.09362 | 4.81113 | 1.01071 |
| 28 | C | 1.04925 | 3.86294 | 1.11167 |
| 29 | C | 1.49752 | 3.45328 | 2.36486 |
| 30 | H | 0.97373 | 3.82659 | 3.2472 |
| 31 | C | 2.6051 | 2.5909 | 2.47964 |
| 32 | H | 2.96894 | 2.2616 | 3.45504 |
| 33 | C | 3.27539 | 2.14579 | 1.34248 |
| 34 | C | 4.46309 | 1.2616 | 1.48694 |
| 35 | C | 2.83532 | 2.54925 | 0.0587 |
| 36 | C | 1.70187 | 3.40624 | −0.05878 |
| 37 | C | −1.78367 | 5.93497 | −0.44187 |
| 38 | H | −2.02657 | 5.87415 | −1.50987 |
| 39 | C | −1.51987 | 7.4071 | −0.08855 |
| 40 | H | −0.64911 | 7.75419 | −0.6681 |
| 41 | H | −1.27717 | 7.48902 | 0.98296 |
| 42 | C | −2.76144 | 8.24859 | −0.42267 |
| 43 | H | −2.58067 | 9.30269 | −0.1561 |
| 44 | H | −2.93905 | 8.21474 | −1.51294 |
| 45 | C | −4.0032 | 7.71687 | 0.30812 |
| 46 | H | −3.85806 | 7.82622 | 1.39835 |
| 47 | H | −4.8923 | 8.30923 | 0.03731 |
| 48 | C | −4.24358 | 6.23482 | −0.01687 |
| 49 | H | −4.45045 | 6.10581 | −1.09109 |
| 50 | H | −5.10491 | 5.84688 | 0.55076 |
| 51 | C | −2.99731 | 5.4197 | 0.36502 |
| 52 | H | −2.79484 | 5.57128 | 1.43262 |
| 53 | C | −3.39447 | 3.40157 | −1.05108 |
| 54 | C | −3.57232 | 1.92526 | −1.12888 |
| 55 | C | −3.71657 | 1.31279 | −2.37153 |
| 56 | H | −3.67927 | 1.94073 | −3.26404 |
| 57 | C | −3.91339 | −0.07869 | −2.46324 |
| 58 | H | −4.03451 | −0.57193 | −3.42982 |
| 59 | C | −3.96461 | −0.8635 | −1.31372 |
| 60 | C | −4.19157 | −2.32906 | −1.43184 |
| 61 | C | −4.12406 | −2.50417 | 1.06669 |
| 62 | C | −3.88222 | −1.03746 | 1.143 |
| 63 | C | −3.74423 | −0.42453 | 2.38593 |
| 64 | H | −3.80311 | −1.05006 | 3.279 |
| 65 | C | −3.54549 | 0.96661 | 2.47719 |
| 66 | H | −3.44608 | 1.46278 | 3.4447 |
| 67 | C | −3.48623 | 1.74998 | 1.32688 |
| 68 | C | −3.31747 | 3.22294 | 1.4481 |
| 69 | C | −3.61509 | 1.14624 | 0.05258 |
| 70 | C | −3.81461 | −0.26254 | −0.04017 |
| 71 | C | −4.28574 | −4.54613 | −0.35472 |
| 72 | H | −4.14727 | −4.73597 | −1.42602 |
| 73 | C | −5.66877 | −5.08436 | 0.04418 |
| 74 | H | −6.43921 | −4.50656 | −0.4917 |
| 75 | H | −5.82272 | −4.94612 | 1.12646 |
| 76 | C | −5.75417 | −6.57434 | −0.32562 |
| 77 | H | −6.74161 | −6.97438 | −0.04366 |
| 78 | H | −5.65997 | −6.67776 | −1.42202 |
| 79 | C | −4.63572 | −7.3772 | 0.35604 |
| 80 | H | −4.68625 | −8.43741 | 0.05931 |
| 81 | H | −4.77895 | −7.33693 | 1.45161 |
| 82 | C | −3.25108 | −6.80276 | 0.01492 |
| 83 | H | −2.46164 | −7.34764 | 0.55763 |
| 84 | H | −3.05212 | −6.89132 | −1.06495 |
| 85 | C | −3.19727 | −5.32234 | 0.42263 |
| 86 | H | −3.41577 | −5.24744 | 1.49501 |
| 87 | C | −1.30913 | −4.56423 | −1.01727 |
| 88 | C | 0.04236 | −3.94824 | −1.11243 |
| 89 | C | 0.59286 | −3.68641 | −2.36453 |
| 90 | H | −0.002 | −3.9244 | −3.24873 |
| 91 | C | 1.88484 | −3.13735 | −2.47662 |
| 92 | H | 2.32913 | −2.92821 | −3.45184 |
| 93 | C | 2.63446 | −2.85592 | −1.33655 |
| 94 | C | 4.00589 | −2.29415 | −1.47539 |
| 95 | C | 4.23943 | −2.3449 | 1.01925 |
| 96 | C | 2.84592 | −2.85752 | 1.11808 |
| 97 | C | 2.29492 | −3.11758 | 2.37034 |
| 98 | H | 2.90231 | −2.91046 | 3.25378 |
| 99 | C | 0.99383 | −3.64475 | 2.48289 |
| 100 | H | 0.55183 | −3.85907 | 3.45801 |
| 101 | C | 0.24226 | −3.92224 | 1.34313 |
| 102 | C | −1.11288 | −4.52207 | 1.48108 |
| 103 | C | 0.78033 | −3.65728 | 0.06037 |
| 104 | C | 2.09295 | −3.11261 | −0.05351 |
| 105 | C | 6.05093 | −1.40091 | −0.41293 |
| 106 | H | 6.12171 | −1.12945 | −1.47349 |
| 107 | C | 7.18151 | −2.39153 | −0.08816 |
| 108 | H | 7.03952 | −3.29813 | −0.69903 |
| 109 | H | 7.12241 | −2.6781 | 0.97363 |
| 110 | C | 8.54163 | −1.74084 | −0.38415 |
| 111 | H | 8.61101 | −1.51553 | −1.46418 |
| 112 | H | 9.35242 | −2.44856 | −0.14661 |
| 113 | C | 8.71066 | −0.44253 | 0.41596 |
| 114 | H | 8.70435 | −0.6794 | 1.49565 |
| 115 | H | 9.68205 | 0.02659 | 0.19065 |
| 116 | C | 7.57241 | 0.54166 | 0.10858 |
| 117 | H | 7.5963 | 0.83109 | −0.95396 |
| 118 | H | 7.67054 | 1.45504 | 0.71773 |
| 119 | C | 6.2212 | −0.11804 | 0.43078 |
| 120 | H | 6.21698 | −0.39383 | 1.49226 |

TABLE 5

Optimized Coordinates of S-Δ Using PBE/6-311G**.

| Atom Number | Atom Symbol | x/Å | y/Å | z/Å |
|---|---|---|---|---|
| 1 | O | 5.3726 | 0.53288 | 1.99496 |
| 2 | O | 0.01695 | 5.08113 | 2.58269 |
| 3 | O | −0.18784 | 5.40807 | −2.00465 |
| 4 | O | 4.90026 | 0.5572 | −2.58772 |
| 5 | O | −3.12873 | 4.38442 | 2.04682 |
| 6 | O | −4.4695 | −2.5191 | 2.52376 |
| 7 | O | −4.3801 | −2.8554 | −2.0689 |
| 8 | O | −2.98192 | 4.03678 | −2.54642 |
| 9 | O | −2.26531 | −4.83388 | 2.04119 |
| 10 | O | 4.37202 | −2.49175 | 2.57588 |
| 11 | O | 4.7835 | −2.6386 | −2.00881 |
| 12 | O | −1.90203 | −4.8105 | −2.54926 |
| 13 | N | 5.05874 | 0.40859 | −0.28616 |
| 14 | N | −0.22088 | 5.13612 | 0.28414 |
| 15 | N | −2.91741 | 4.21624 | −0.24229 |
| 16 | N | −4.28362 | −2.7449 | 0.23058 |
| 17 | N | −2.16187 | −4.67551 | −0.25569 |
| 18 | N | 4.55421 | −2.40453 | 0.2733 |
| 19 | C | 4.73775 | 0.88167 | 1.00446 |
| 20 | C | 3.59033 | 1.82384 | 1.10861 |
| 21 | C | 3.15967 | 2.24873 | 2.36289 |
| 22 | H | 3.66654 | 1.85065 | 3.24427 |
| 23 | C | 2.10214 | 3.17143 | 2.47948 |
| 24 | H | 1.75154 | 3.51141 | 3.45611 |
| 25 | C | 1.484 | 3.68593 | 1.34219 |
| 26 | C | 0.38315 | 4.67687 | 1.48599 |
| 27 | C | 0.25391 | 4.83942 | −1.01127 |
| 28 | C | 1.31374 | 3.79926 | −1.11362 |
| 29 | C | 1.74287 | 3.37189 | −2.36769 |
| 30 | H | 1.26677 | 3.80349 | −3.25041 |
| 31 | C | 2.77073 | 2.41577 | −2.48279 |
| 32 | H | 3.11697 | 2.07084 | −3.45928 |
| 33 | C | 3.38277 | 1.89434 | −1.34515 |
| 34 | C | 4.4904 | 0.91054 | −1.48876 |
| 35 | C | 2.96232 | 2.31632 | −0.06057 |
| 36 | C | 1.90639 | 3.2672 | 0.05699 |
| 37 | C | −1.35459 | 6.08117 | 0.43588 |
| 38 | H | −1.60335 | 6.04004 | 1.50366 |
| 39 | C | −0.97888 | 7.5282 | 0.0813 |
| 40 | H | −0.73537 | 7.59265 | −0.99104 |
| 41 | H | −0.08192 | 7.80835 | 0.65723 |
| 42 | C | −2.15126 | 8.46162 | 0.4194 |

TABLE 5-continued

Optimized Coordinates of S-Δ Using PBE/6-311G**.

| Atom Number | Atom Symbol | x/Å | y/Å | z/Å |
|---|---|---|---|---|
| 43 | H | −1.88888 | 9.49988 | 0.15824 |
| 44 | H | −2.33102 | 8.43542 | 1.50955 |
| 45 | C | −3.43015 | 8.03022 | −0.31385 |
| 46 | H | −4.27116 | 8.68753 | −0.03924 |
| 47 | H | −3.27671 | 8.13558 | −1.40335 |
| 48 | C | −3.7842 | 6.57021 | 0.0061 |
| 49 | H | −4.67042 | 6.25192 | −0.56656 |
| 50 | H | −4.00701 | 6.45661 | 1.07898 |
| 51 | C | −2.60341 | 5.66098 | −0.37284 |
| 52 | H | −2.38932 | 5.79912 | −1.43998 |
| 53 | C | −3.13783 | 3.67821 | 1.04355 |
| 54 | C | −3.38473 | 2.21256 | 1.12552 |
| 55 | C | −3.55529 | 1.61137 | 2.37021 |
| 56 | H | −3.48408 | 2.23903 | 3.26081 |
| 57 | C | −3.82271 | 0.23209 | 2.46549 |
| 58 | H | −3.96822 | −0.25234 | 3.43314 |
| 59 | C | −3.92115 | −0.55053 | 1.31761 |
| 60 | C | −4.24263 | −1.9977 | 1.439 |
| 61 | C | −4.19051 | −2.18269 | −1.06016 |
| 62 | C | −3.85438 | −0.7349 | −1.13859 |
| 63 | C | −3.68477 | −0.13335 | −2.38322 |
| 64 | H | −3.78127 | −0.75622 | −3.27486 |
| 65 | C | −3.41114 | 1.24472 | −2.47806 |
| 66 | H | −3.28542 | 1.73304 | −3.44653 |
| 67 | C | −3.30907 | 2.02645 | −1.32983 |
| 68 | C | −3.05838 | 3.48732 | −1.45451 |
| 69 | C | −3.46812 | 1.43389 | −0.05388 |
| 70 | C | −3.74147 | 0.03785 | 0.04237 |
| 71 | C | −4.5673 | −4.19349 | 0.36561 |
| 72 | H | −4.45623 | −4.39359 | 1.43811 |
| 73 | C | −6.00274 | −4.55698 | −0.049 |
| 74 | H | −6.12612 | −4.38604 | −1.13063 |
| 75 | H | −6.70251 | −3.89578 | 0.48769 |
| 76 | C | −6.2786 | −6.0288 | 0.29752 |
| 77 | H | −6.22335 | −6.15631 | 1.39381 |
| 78 | H | −7.3019 | −6.30083 | −0.00891 |
| 79 | C | −5.25422 | −6.95733 | −0.37148 |
| 80 | H | −5.36755 | −6.89177 | −1.46879 |
| 81 | H | −5.44077 | −8.00548 | −0.08664 |
| 82 | C | −3.8188 | −6.56091 | 0.00377 |
| 83 | H | −3.65774 | −6.67022 | 1.08811 |
| 84 | H | −3.08619 | −7.19832 | −0.52152 |
| 85 | C | −3.57592 | −5.09644 | −0.40316 |
| 86 | H | −3.7769 | −4.99893 | −1.47687 |
| 87 | C | −1.61766 | −4.54545 | 1.03932 |
| 88 | C | −0.21992 | −4.04111 | 1.13123 |
| 89 | C | 0.35104 | −3.81643 | 2.38148 |
| 90 | H | −0.25746 | −4.00664 | 3.26798 |
| 91 | C | 1.67929 | −3.36009 | 2.4889 |
| 92 | H | 2.13971 | −3.17908 | 3.46233 |
| 93 | C | 2.44347 | −3.13139 | 1.34688 |
| 94 | C | 3.84852 | −2.65745 | 1.48098 |
| 95 | C | 4.06997 | −2.7208 | −1.01387 |
| 96 | C | 2.64906 | −3.15279 | −1.10808 |
| 97 | C | 2.08091 | −3.38244 | −2.35863 |
| 98 | H | 2.69844 | −3.21785 | −3.24395 |
| 99 | C | 0.74746 | −3.82224 | −2.46661 |
| 100 | H | 0.28942 | −4.01051 | −3.43973 |
| 101 | C | −0.01985 | −4.04108 | −1.32487 |
| 102 | C | −1.41695 | −4.5354 | −1.45912 |
| 103 | C | 0.53585 | −3.80797 | −0.04347 |
| 104 | C | 1.88332 | −3.35474 | 0.06561 |
| 105 | C | 5.92898 | −1.85968 | 0.40941 |
| 106 | H | 6.01743 | −1.59197 | 1.46944 |
| 107 | C | 7.01471 | −2.89868 | 0.08117 |
| 108 | H | 6.83493 | −3.7971 | 0.69421 |
| 109 | H | 6.9399 | −3.18519 | −0.97981 |
| 110 | C | 8.40245 | −2.30745 | 0.37269 |
| 111 | H | 9.18073 | −3.05045 | 0.13402 |
| 112 | H | 8.4846 | −2.08455 | 1.45236 |
| 113 | C | 8.62701 | −1.01869 | −0.42918 |
| 114 | H | 9.61817 | −0.59248 | −0.20506 |
| 115 | H | 8.60867 | −1.25636 | −1.50848 |
| 116 | C | 7.53257 | 0.01364 | −0.12113 |
| 117 | H | 7.5718 | 0.30388 | 0.94099 |
| 118 | H | 7.66772 | 0.92127 | −0.732 |
| 119 | C | 6.15203 | −0.58622 | −0.43621 |
| 120 | H | 6.12779 | −0.8621 | −1.49768 |

TABLE 6

Optimized Coordinates of the (RS)-Dimer Using PBE/6-311G**.

| Atom Number | Atom Symbol | x/Å | y/Å | z/Å |
|---|---|---|---|---|
| 1 | O | −5.7415 | −5.47905 | −0.70242 |
| 2 | O | −6.38613 | −0.03263 | −5.11984 |
| 3 | O | −1.80182 | 0.4228 | −5.25373 |
| 4 | O | −1.17196 | −5.19616 | −0.99689 |
| 5 | O | −6.00945 | 2.93662 | −4.30983 |
| 6 | O | −6.48576 | 3.74334 | 2.66455 |
| 7 | O | −1.9004 | 4.14485 | 2.94902 |
| 8 | O | −1.47115 | 3.53927 | −4.0941 |
| 9 | O | −5.93398 | 1.80692 | 4.99815 |
| 10 | O | −6.2812 | −4.69457 | 2.29231 |
| 11 | O | −1.67786 | −4.93601 | 2.26718 |
| 12 | O | −1.35451 | 1.57278 | 5.02411 |
| 13 | N | −3.45158 | −5.22352 | −0.67947 |
| 14 | N | −4.09419 | 0.28101 | −5.12527 |
| 15 | N | −3.70944 | 3.00868 | −4.18546 |
| 16 | N | −4.18432 | 3.89419 | 2.84527 |
| 17 | N | −3.63633 | 1.78551 | 4.80293 |
| 18 | N | −3.97398 | −4.80036 | 2.17093 |
| 19 | C | −4.7549 | −4.85216 | −1.07509 |
| 20 | C | −4.86871 | −3.66192 | −1.95959 |
| 21 | C | −6.13042 | −3.18949 | −2.31557 |
| 22 | H | −7.00573 | −3.69813 | −1.9063 |
| 23 | C | −6.26042 | −2.09863 | −3.19457 |
| 24 | H | −7.24169 | −1.73068 | −3.50118 |
| 25 | C | −5.12903 | −1.4742 | −3.7164 |
| 26 | C | −5.28729 | −0.36745 | −4.69583 |
| 27 | C | −2.79234 | −0.14841 | −4.79997 |
| 28 | C | −2.67509 | −1.32088 | −3.89222 |
| 29 | C | −1.41779 | −1.83831 | −3.59243 |
| 30 | H | −0.53334 | −1.39948 | −4.06022 |
| 31 | C | −1.28596 | −2.95234 | −2.73775 |
| 32 | H | −0.29769 | −3.37878 | −2.54559 |
| 33 | C | −2.4133 | −3.53579 | −2.16223 |
| 34 | C | −2.26633 | −4.69999 | −1.25207 |
| 35 | C | −3.70528 | −3.03999 | −2.47344 |
| 36 | C | −3.8377 | −1.92724 | −3.35513 |
| 37 | C | −4.27012 | 1.41482 | −6.0668 |
| 38 | H | −5.35155 | 1.59827 | −6.06806 |
| 39 | C | −3.83495 | 1.0689 | −7.49898 |
| 40 | H | −4.31782 | 0.12465 | −7.7985 |
| 41 | H | −2.74274 | 0.92188 | −7.52549 |
| 42 | C | −4.2466 | 2.20852 | −8.44395 |
| 43 | H | −3.92749 | 1.97479 | −9.47289 |
| 44 | H | −5.34902 | 2.28412 | −8.45607 |
| 45 | C | −3.64987 | 3.55013 | −7.99203 |
| 46 | H | −2.54874 | 3.50312 | −8.07701 |
| 47 | H | −3.99098 | 4.36418 | −8.65219 |
| 48 | C | −4.02138 | 3.8669 | −6.53469 |
| 49 | H | −5.11097 | 3.99509 | −6.42839 |
| 50 | H | −3.52882 | 4.79494 | −6.20245 |
| 51 | C | −3.55709 | 2.71443 | −5.63026 |
| 52 | H | −2.47713 | 2.58089 | −5.76907 |
| 53 | C | −5.00138 | 3.02121 | −3.61608 |
| 54 | C | −5.07166 | 3.13493 | −2.13543 |
| 55 | C | −6.3051 | 3.03026 | −1.49523 |
| 56 | H | −7.19027 | 2.84276 | −2.10677 |
| 57 | C | −6.39842 | 3.1894 | −0.10065 |
| 58 | H | −7.35988 | 3.13653 | 0.41391 |
| 59 | C | −5.25825 | 3.44666 | 0.65802 |
| 60 | C | −5.39125 | 3.69661 | 2.11663 |
| 61 | C | −2.90362 | 3.96478 | 2.26028 |
| 62 | C | −2.82558 | 3.82293 | 0.78144 |
| 63 | C | −1.60689 | 4.00435 | 0.13229 |
| 64 | H | −0.72282 | 4.2771 | 0.71324 |

TABLE 6-continued

Optimized Coordinates of the (RS)-Dimer Using PBE/6-311G**.

| Atom Number | Atom Symbol | x/Å | y/Å | z/Å |
|---|---|---|---|---|
| 65 | C | −1.5157 | 3.8787 | −1.26956 |
| 66 | H | −0.56254 | 4.06321 | −1.77302 |
| 67 | C | −2.64115 | 3.54853 | −2.02249 |
| 68 | C | −2.53065 | 3.37921 | −3.49375 |
| 69 | C | −3.89837 | 3.38786 | −1.38416 |
| 70 | C | −3.99296 | 3.5405 | 0.02981 |
| 71 | C | −4.33385 | 4.15939 | 4.29858 |
| 72 | H | −5.40077 | 3.99507 | 4.49299 |
| 73 | C | −3.99701 | 5.61536 | 4.65905 |
| 74 | H | −4.56882 | 6.28273 | 3.99366 |
| 75 | H | −2.92332 | 5.80206 | 4.49299 |
| 76 | C | −4.35877 | 5.87758 | 6.12942 |
| 77 | H | −4.11978 | 6.92081 | 6.39342 |
| 78 | H | −5.44829 | 5.74848 | 6.2634 |
| 79 | C | −3.61626 | 4.90487 | 7.05633 |
| 80 | H | −3.89538 | 5.0823 | 8.10758 |
| 81 | H | −2.52873 | 5.08504 | 6.97178 |
| 82 | C | −3.91322 | 3.44795 | 6.67576 |
| 83 | H | −3.33532 | 2.75395 | 7.30753 |
| 84 | H | −4.98415 | 3.22485 | 6.80625 |
| 85 | C | −3.52269 | 3.20772 | 5.20599 |
| 86 | H | −2.45778 | 3.44068 | 5.08821 |
| 87 | C | −4.91816 | 1.2085 | 4.6607 |
| 88 | C | −4.96833 | −0.15305 | 4.06493 |
| 89 | C | −6.20121 | −0.7229 | 3.75416 |
| 90 | H | −7.10292 | −0.13806 | 3.94757 |
| 91 | C | −6.27006 | −2.02195 | 3.2175 |
| 92 | H | −7.22853 | −2.48855 | 2.98128 |
| 93 | C | −5.10623 | −2.75338 | 2.98749 |
| 94 | C | −5.202 | −4.14221 | 2.46517 |
| 95 | C | −2.70012 | −4.28883 | 2.49092 |
| 96 | C | −2.65001 | −2.93146 | 3.09795 |
| 97 | C | −1.42724 | −2.3939 | 3.49198 |
| 98 | H | −0.52082 | −2.99612 | 3.40125 |
| 99 | C | −1.35576 | −1.09559 | 4.03876 |
| 100 | H | −0.39358 | −0.69091 | 4.36531 |
| 101 | C | −2.51098 | −0.33006 | 4.18688 |
| 102 | C | −2.4243 | 1.05981 | 4.70562 |
| 103 | C | −3.77261 | −0.87689 | 3.83837 |
| 104 | C | −3.84315 | −2.19219 | 3.29355 |
| 105 | C | −4.08444 | −6.1607 | 1.58433 |
| 106 | H | −5.14993 | −6.27108 | 1.34859 |
| 107 | C | −3.69144 | −7.26147 | 2.58424 |
| 108 | H | −4.26949 | −7.11525 | 3.51145 |
| 109 | H | −2.62074 | −7.16946 | 2.82883 |
| 110 | C | −3.98239 | −8.64188 | 1.97466 |
| 111 | H | −5.06969 | −8.73851 | 1.80022 |
| 112 | H | −3.69647 | −9.4322 | 2.68792 |
| 113 | C | −3.2398 | −8.82408 | 0.64425 |
| 114 | H | −2.15054 | −8.80007 | 0.83094 |
| 115 | H | −3.47401 | −9.8069 | 0.20421 |
| 116 | C | −3.60484 | −7.70682 | −0.34418 |
| 117 | H | −4.67832 | −7.74911 | −0.59106 |
| 118 | H | −3.03091 | −7.81045 | −1.27951 |
| 119 | C | −3.27672 | −6.34101 | 0.28138 |
| 120 | H | −2.20819 | −6.32379 | 0.52722 |
| 121 | O | 5.74044 | 5.49435 | 0.71445 |
| 122 | O | 6.3908 | 0.03446 | 5.11345 |
| 123 | O | 1.80676 | −0.42436 | 5.24824 |
| 124 | O | 1.17153 | 5.20062 | 0.99931 |
| 125 | O | 6.01265 | −2.94208 | 4.30506 |
| 126 | O | 6.48669 | −3.79222 | −2.66607 |
| 127 | O | 1.8974 | −4.13479 | −2.95389 |
| 128 | O | 1.47243 | −3.5324 | 4.08921 |
| 129 | O | 5.93656 | −1.81437 | −4.96572 |
| 130 | O | 6.27719 | 4.69508 | −2.27933 |
| 131 | O | 1.67380 | 4.93944 | −2.27092 |
| 132 | O | 1.35713 | −1.5688 | −5.02891 |
| 133 | N | 3.4513 | 5.23111 | 0.6833 |
| 134 | N | 4.09898 | −0.28017 | 5.11989 |
| 135 | N | 3.71261 | −3.00908 | 4.18012 |
| 136 | N | 4.18333 | −3.90659 | −2.84915 |
| 137 | N | 3.63736 | −1.78589 | −4.79381 |
| 138 | N | 3.96974 | 4.80302 | −2.16629 |
| 139 | C | 4.75483 | 4.86218 | 1.08071 |
| 140 | C | 4.86972 | 3.67071 | 1.96327 |
| 141 | C | 6.13189 | 3.19971 | 2.31944 |
| 142 | H | 7.00669 | 3.71072 | 1.91205 |
| 143 | C | 6.26291 | 2.10677 | 3.19565 |
| 144 | H | 7.2445 | 1.73938 | 3.50191 |
| 145 | C | 5.13206 | 1.47934 | 3.71502 |
| 146 | C | 5.29144 | 0.36995 | 4.69125 |
| 147 | C | 2.79667 | 0.14885 | 4.79567 |
| 148 | C | 2.6782 | 1.3224 | 3.88929 |
| 149 | C | 1.42035 | 1.83871 | 3.58963 |
| 150 | H | 0.53623 | 1.39821 | 4.05637 |
| 151 | C | 1.28741 | 2.95408 | 2.73682 |
| 152 | H | 0.29872 | 3.3795 | 2.54424 |
| 153 | C | 2.4143 | 3.54021 | 2.1632 |
| 154 | C | 2.26633 | 4.70533 | 1.25438 |
| 155 | C | 3.7068 | 3.04578 | 2.47458 |
| 156 | C | 3.84028 | 1.93145 | 3.35412 |
| 157 | C | 4.27619 | −1.41472 | 6.06037 |
| 158 | H | 5.35749 | −1.59895 | 6.05927 |
| 159 | C | 3.84408 | −1.06837 | 7.49344 |
| 160 | H | 2.75219 | −0.91924 | 7.5217 |
| 161 | H | 4.3292 | −0.12502 | 7.7922 |
| 162 | C | 4.25486 | −2.20864 | 8.4379 |
| 163 | H | 3.9379 | −1.97402 | 9.46731 |
| 164 | H | 5.35712 | −2.28674 | 8.44822 |
| 165 | C | 3.65437 | −3.54885 | 7.98696 |
| 166 | H | 3.9942 | −4.36361 | 8.6469 |
| 167 | H | 2.55344 | −3.49913 | 8.07301 |
| 168 | C | 4.02397 | −3.86654 | 6.5294 |
| 169 | H | 3.52941 | −4.79374 | 6.19776 |
| 170 | H | 5.11321 | −3.99687 | 6.42242 |
| 171 | C | 3.56115 | −2.71351 | 5.62481 |
| 172 | H | 2.48145 | −2.57832 | 5.76402 |
| 173 | C | 5.00474 | −3.02807 | 3.61123 |
| 174 | C | 5.07552 | −3.15015 | 2.13114 |
| 175 | C | 6.31039 | −3.05921 | 1.49425 |
| 176 | H | 7.1968 | −2.8771 | 2.10285 |
| 177 | C | 6.40346 | −3.22483 | 0.09755 |
| 178 | H | 7.36592 | −3.18368 | −0.41623 |
| 179 | C | 5.26145 | −3.47269 | −0.66139 |
| 180 | C | 5.39256 | −3.72765 | −2.1194 |
| 181 | C | 2.90219 | −3.96629 | −2.26445 |
| 182 | C | 2.82533 | −3.82542 | −0.78559 |
| 183 | C | 1.60524 | −3.99727 | −0.13662 |
| 184 | H | 0.7194 | −4.26459 | −0.71723 |
| 185 | C | 1.51477 | −3.87029 | 1.26505 |
| 186 | H | 0.5606 | −4.04912 | 1.76857 |
| 187 | C | 2.64217 | −3.54664 | 2.01776 |
| 188 | C | 2.53243 | −3.37607 | 3.48879 |
| 189 | C | 3.90081 | −3.39604 | 1.37975 |
| 190 | C | 3.99484 | −3.55241 | −0.03386 |
| 191 | C | 4.3294 | −4.1661 | −4.30346 |
| 192 | H | 5.3972 | −4.00883 | −4.4984 |
| 193 | C | 3.98116 | −5.61745 | −4.67177 |
| 194 | H | 2.90575 | −5.79568 | −4.50778 |
| 195 | H | 4.54663 | −6.29312 | −4.00936 |
| 196 | C | 4.34345 | −5.87475 | −6.14311 |
| 197 | H | 5.43465 | −5.75654 | −6.27326 |
| 198 | H | 4.0944 | −6.91391 | −6.41382 |
| 199 | C | 3.61412 | −4.88927 | −7.06728 |
| 200 | H | 2.52461 | −5.06007 | −6.98949 |
| 201 | H | 3.89714 | −5.06233 | −8.11822 |
| 202 | C | 3.92083 | −3.43717 | −6.67553 |
| 203 | H | 4.9942 | −3.22123 | −6.79808 |
| 204 | H | 3.35171 | −2.73458 | −7.30574 |
| 205 | C | 3.5239 | −3.20537 | −5.20628 |
| 206 | H | 2.45805 | −3.43723 | −5.09498 |
| 207 | C | 4.91912 | −1.21251 | −4.63902 |
| 208 | C | 4.96763 | 0.14981 | −4.04465 |
| 209 | C | 6.19958 | 0.71882 | −3.72858 |
| 210 | H | 7.10163 | 0.13266 | −3.91632 |
| 211 | C | 6.26736 | 2.01916 | −3.19492 |
| 212 | H | 7.22523 | 2.4854 | −2.9556 |
| 213 | C | 5.10329 | 2.75243 | −2.97215 |
| 214 | C | 5.19818 | 4.14289 | −2.45396 |
| 215 | C | 2.69656 | 4.29074 | −2.48804 |
| 216 | C | 2.64784 | 2.9324 | −3.09299 |

TABLE 6-continued

Optimized Coordinates of the (RS)-Dimer Using PBE/6-311G**.

| Atom Number | Atom Symbol | x/Å | y/Å | z/Å |
|---|---|---|---|---|
| 217 | C | 1.42614 | 2.3953 | −3.4908 |
| 218 | H | 0.52006 | 2.99848 | −3.403 |
| 219 | C | 1.35591 | 1.0968 | −4.0373 |
| 220 | H | 0.3949 | 0.69277 | −4.36808 |
| 221 | C | 2.51116 | 0.33021 | −4.18017 |
| 222 | C | 2.4257 | −1.05842 | −4.70238 |
| 223 | C | 3.77169 | 0.87566 | −3.82565 |
| 224 | C | 3.84106 | 2.19175 | −3.28247 |
| 225 | C | 4.07965 | 6.16502 | −1.58316 |
| 226 | H | 5.14562 | 6.27699 | −1.35039 |
| 227 | C | 3.68343 | 7.26357 | −2.58414 |
| 228 | H | 4.25864 | 7.11554 | −3.51284 |
| 229 | H | 2.61196 | 7.1712 | −2.82522 |
| 230 | C | 3.97645 | 8.64504 | −1.97788 |
| 231 | H | 3.68827 | 9.4341 | −2.69163 |
| 232 | H | 5.06435 | 8.74186 | −1.80729 |
| 233 | C | 3.23841 | 8.82992 | −0.64523 |
| 234 | H | 3.47452 | 9.81342 | −0.20771 |
| 235 | H | 2.14854 | 8.80616 | −0.82832 |
| 236 | C | 3.60595 | 7.71423 | 0.34414 |
| 237 | H | 4.6802 | 7.75635 | 0.58768 |
| 238 | H | 3.03481 | 7.81959 | 1.28097 |
| 239 | C | 3.27534 | 6.34776 | −0.27835 |
| 240 | H | 2.20625 | 6.33106 | −0.5216 |

TABLE 7

Optimized Coordinates of the (RR)-Dimer Using PBE/6-311G**.

| Atom Number | Atom Symbol | x/Å | y/Å | z/Å |
|---|---|---|---|---|
| 1 | O | −5.86015 | −5.38639 | −0.60631 |
| 2 | O | −6.36431 | −0.03957 | −5.16036 |
| 3 | O | −1.76911 | 0.33179 | −5.26851 |
| 4 | O | −1.28957 | −5.23085 | −0.91492 |
| 5 | O | −5.96005 | 2.93948 | −4.36473 |
| 6 | O | −6.42141 | 4.25907 | 2.53659 |
| 7 | O | −1.82224 | 4.25257 | 2.87091 |
| 8 | O | −1.41229 | 3.45929 | −4.15532 |
| 9 | O | −5.97206 | 2.13651 | 4.72337 |
| 10 | O | −6.38357 | −4.48208 | 2.33267 |
| 11 | O | −1.78164 | −4.79265 | 2.34616 |
| 12 | O | −1.41814 | 1.74004 | 5.05003 |
| 13 | N | −3.56546 | −5.18164 | −0.58496 |
| 14 | N | −4.06746 | 0.2375 | −5.15 |
| 15 | N | −3.6602 | 2.97634 | −4.23571 |
| 16 | N | −4.11937 | 4.16913 | 2.74986 |
| 17 | N | −3.67132 | 2.02591 | 4.68446 |
| 18 | N | −4.07722 | −4.63209 | 2.23925 |
| 19 | C | −4.85919 | −4.79255 | −0.99388 |
| 20 | C | −4.94339 | −3.62277 | −1.91005 |
| 21 | C | −6.19199 | −3.12606 | −2.277 |
| 22 | H | −7.08075 | −3.60099 | −1.85647 |
| 23 | C | −6.29163 | −2.05294 | −3.18149 |
| 24 | H | −7.26229 | −1.66615 | −3.49829 |
| 25 | C | −5.14411 | −1.46995 | −3.71568 |
| 26 | C | −5.27505 | −0.38355 | −4.71986 |
| 27 | C | −2.77438 | −0.21495 | −4.81655 |
| 28 | C | −2.68517 | −1.38223 | −3.897 |
| 29 | C | −1.44282 | −1.93238 | −3.58776 |
| 30 | H | −0.541 | −1.53055 | −4.05697 |
| 31 | C | −1.34524 | −3.02726 | −2.70449 |
| 32 | H | −0.3727 | −3.4823 | −2.50209 |
| 33 | C | −2.4876 | −3.56496 | −2.11669 |
| 34 | C | −2.36972 | −4.70966 | −1.17868 |
| 35 | C | −3.7647 | −3.04315 | −2.43933 |
| 36 | C | −3.86409 | −1.94683 | −3.3455 |
| 37 | C | −4.22591 | 1.36276 | −6.10379 |
| 38 | H | −5.30557 | 1.55595 | −6.1142 |
| 39 | C | −3.78528 | 0.99951 | −7.5302 |
| 40 | H | −4.27326 | 0.05556 | −7.82233 |
| 41 | H | −2.69406 | 0.84464 | −7.54954 |
| 42 | C | −4.18395 | 2.13211 | −8.48894 |
| 43 | H | −3.8618 | 1.88561 | −9.51392 |
| 44 | H | −5.28563 | 2.21554 | −8.50676 |
| 45 | C | −3.57972 | 3.4738 | −8.047 |
| 46 | H | −2.47867 | 3.41837 | −8.12718 |
| 47 | H | −3.91252 | 4.28395 | −8.71608 |
| 48 | C | −3.95551 | 3.80672 | −6.59449 |
| 49 | H | −5.04467 | 3.94471 | −6.49514 |
| 50 | H | −3.45713 | 4.73403 | −6.26908 |
| 51 | C | −3.50567 | 2.65978 | −5.67569 |
| 52 | H | −2.42646 | 2.51554 | −5.80884 |
| 53 | C | −4.95287 | 3.04549 | −3.67259 |
| 54 | C | −5.02614 | 3.25324 | −2.20064 |
| 55 | C | −6.26764 | 3.26603 | −1.56807 |
| 56 | H | −7.16004 | 3.10081 | −2.17541 |
| 57 | C | −6.35776 | 3.51451 | −0.18616 |
| 58 | H | −7.32381 | 3.56234 | 0.3203 |
| 59 | C | −5.20765 | 3.73171 | 0.56999 |
| 60 | C | −5.33225 | 4.07068 | 2.01031 |
| 61 | C | −2.8315 | 4.13131 | 2.17743 |
| 62 | C | −2.75337 | 3.94299 | 0.70338 |
| 63 | C | −1.5231 | 4.0236 | 0.05337 |
| 64 | H | −0.62227 | 4.2659 | 0.62396 |
| 65 | C | −1.44017 | 3.83497 | −1.34158 |
| 66 | H | −0.48513 | 3.96111 | −1.85719 |
| 67 | C | −2.57967 | 3.53889 | −2.08489 |
| 68 | C | −2.47364 | 3.33381 | −3.55077 |
| 69 | C | −3.84554 | 3.4764 | −1.45089 |
| 70 | C | −3.93368 | 3.70239 | −0.04624 |
| 71 | C | −4.26574 | 4.44163 | 4.19988 |
| 72 | H | −5.34295 | 4.34782 | 4.38351 |
| 73 | C | −3.83287 | 5.86713 | 4.58075 |
| 74 | H | −4.33733 | 6.58081 | 3.90928 |
| 75 | H | −2.74469 | 5.97215 | 4.44091 |
| 76 | C | −4.21426 | 6.14193 | 6.04478 |
| 77 | H | −3.89569 | 7.15778 | 6.33073 |
| 78 | H | −5.31443 | 6.10774 | 6.14145 |
| 79 | C | −3.5906 | 5.10095 | 6.98647 |
| 80 | H | −3.90676 | 5.28397 | 8.02624 |
| 81 | H | −2.49026 | 5.19981 | 6.95826 |
| 82 | C | −3.96763 | 3.6725 | 6.5678 |
| 83 | H | −3.46276 | 2.93381 | 7.21104 |
| 84 | H | −5.05562 | 3.51582 | 6.64651 |
| 85 | C | −3.5282 | 3.4377 | 5.11234 |
| 86 | H | −2.45151 | 3.63354 | 5.0416 |
| 87 | C | −4.95976 | 1.49111 | 4.47104 |
| 88 | C | −5.02178 | 0.10824 | 3.92271 |
| 89 | C | −6.2567 | −0.44822 | 3.59728 |
| 90 | H | −7.15198 | 0.16023 | 3.74115 |
| 91 | C | −6.33687 | −1.76807 | 3.11534 |
| 92 | H | −7.29816 | −2.22777 | 2.8774 |
| 93 | C | −5.18276 | −2.53029 | 2.94416 |
| 94 | C | −5.29653 | −3.94044 | 2.48889 |
| 95 | C | −2.79639 | −4.12564 | 2.54346 |
| 96 | C | −2.73107 | −2.74949 | 3.10779 |
| 97 | C | −1.50632 | −2.21704 | 3.50595 |
| 98 | H | −0.60179 | −2.82777 | 3.44252 |
| 99 | C | −1.43013 | −0.90627 | 4.02093 |
| 100 | H | −0.4726 | −0.50657 | 4.36443 |
| 101 | C | −2.57568 | −0.12165 | 4.12886 |
| 102 | C | −2.47899 | 1.26249 | 4.65746 |
| 103 | C | −3.83673 | −0.65018 | 3.75796 |
| 104 | C | −3.91542 | −1.98213 | 3.25519 |
| 105 | C | −4.20858 | −6.01544 | 1.71463 |
| 106 | H | −5.27712 | −6.12182 | 1.49088 |
| 107 | C | −3.82527 | −7.07821 | 2.7579 |
| 108 | H | −4.39165 | −6.88225 | 3.68305 |
| 109 | H | −2.75068 | −6.99605 | 2.98882 |
| 110 | C | −4.14862 | −8.47698 | 2.21068 |
| 111 | H | −5.23932 | −8.55997 | 2.05163 |
| 112 | H | −3.87016 | −9.24167 | 2.95414 |
| 113 | C | −3.42367 | −8.73198 | 0.88151 |
| 114 | H | −2.33254 | −8.72628 | 1.05796 |
| 115 | H | −3.68526 | −9.72639 | 0.4852 |
| 116 | C | −3.77071 | −7.6483 | −0.15073 |
| 117 | H | −4.84579 | −7.67816 | −0.3923 |
| 118 | H | −3.20268 | −7.80103 | −1.08285 |

TABLE 7-continued

Optimized Coordinates of the (RR)-Dimer Using PBE/6-311G**.

| Atom Number | Atom Symbol | x/Å | y/Å | z/Å |
|---|---|---|---|---|
| 119 | C | −3.41192 | −6.2653 | 0.41687 |
| 120 | H | −2.34208 | −6.2606 | 0.65804 |
| 121 | O | 6.47811 | −1.4608 | −4.57332 |
| 122 | O | 5.84886 | 5.04662 | −1.96556 |
| 123 | O | 1.30335 | 4.8272 | −2.45832 |
| 124 | O | 1.8856 | −1.79391 | −4.89432 |
| 125 | O | 6.29935 | 4.97182 | 1.06189 |
| 126 | O | 5.90095 | −0.62578 | 5.31039 |
| 127 | O | 1.33215 | −0.27331 | 5.3666 |
| 128 | O | 1.69374 | 5.19847 | 0.89281 |
| 129 | O | 6.42455 | −3.26265 | 3.81211 |
| 130 | O | 6.03287 | −4.13238 | −3.16602 |
| 131 | O | 1.46496 | −4.41735 | −2.88499 |
| 132 | O | 1.82091 | −3.35658 | 4.10012 |
| 133 | N | 4.17788 | −1.68337 | −4.68583 |
| 134 | N | 3.5524 | 4.85303 | −1.98076 |
| 135 | N | 3.99342 | 5.06163 | 0.89274 |
| 136 | N | 3.60114 | −0.59453 | 5.17271 |
| 137 | N | 4.11774 | −3.20267 | 3.97493 |
| 138 | N | 3.73251 | −4.0716 | −3.06565 |
| 139 | C | 2.71105 | 4.63272 | 1.29209 |
| 140 | C | 5.37274 | −0.98479 | −4.34862 |
| 141 | C | 5.20994 | 0.35339 | −3.72377 |
| 142 | C | 6.33829 | 1.05712 | −3.30563 |
| 143 | H | 7.31378 | 0.57837 | −3.41161 |
| 144 | C | 6.21559 | 2.35935 | −2.787 |
| 145 | H | 7.08999 | 2.92972 | −2.46687 |
| 146 | C | 4.96399 | 2.96304 | −2.69191 |
| 147 | C | 4.85819 | 4.36012 | −2.1925 |
| 148 | C | 2.38223 | 4.24186 | −2.49169 |
| 149 | C | 2.52577 | 2.87269 | −3.04872 |
| 150 | C | 1.40731 | 2.19431 | −3.52766 |
| 151 | H | 0.43606 | 2.69561 | −3.53713 |
| 152 | C | 1.52758 | 0.88127 | −4.02792 |
| 153 | H | 0.6458 | 0.36597 | −4.41813 |
| 154 | C | 2.76852 | 0.24812 | −4.05921 |
| 155 | C | 2.87937 | −1.14344 | −4.57378 |
| 156 | C | 3.92636 | 0.94023 | −3.62039 |
| 157 | C | 3.80327 | 2.26212 | −3.10118 |
| 158 | C | 3.36825 | 6.16178 | −1.30953 |
| 159 | H | 2.29358 | 6.21511 | −1.09926 |
| 160 | C | 3.74579 | 7.35365 | −2.20289 |
| 161 | H | 4.82682 | 7.32173 | −2.4136 |
| 162 | H | 3.20404 | 7.25849 | −3.15786 |
| 163 | C | 3.37141 | 8.66622 | −1.49511 |
| 164 | H | 3.64891 | 9.52577 | −2.12668 |
| 165 | H | 2.27472 | 8.70046 | −1.36066 |
| 166 | C | 4.04929 | 8.76502 | −0.12073 |
| 167 | H | 3.75078 | 9.69492 | 0.38987 |
| 168 | H | 5.14517 | 8.80461 | −0.25922 |
| 169 | C | 3.69929 | 7.55219 | 0.75386 |
| 170 | H | 2.61585 | 7.52256 | 0.95402 |
| 171 | H | 4.22594 | 7.60626 | 1.72056 |
| 172 | C | 4.12674 | 6.264 | 0.03211 |
| 173 | H | 5.20127 | 6.32904 | −0.17877 |
| 174 | C | 5.21388 | 4.47956 | 1.34234 |
| 175 | C | 5.10249 | 3.2546 | 2.1745 |
| 176 | C | 6.26076 | 2.59523 | 2.58278 |
| 177 | H | 7.22259 | 2.98116 | 2.2393 |
| 178 | C | 6.18332 | 1.47914 | 3.43612 |
| 179 | H | 7.08108 | 0.95988 | 3.77764 |
| 180 | C | 4.947 | 1.02501 | 3.8897 |
| 181 | C | 4.8878 | −0.11811 | 4.84111 |
| 182 | C | 2.39851 | 0.09265 | 4.87977 |
| 183 | C | 2.49357 | 1.25663 | 3.96385 |
| 184 | C | 1.34272 | 1.95478 | 3.60652 |
| 185 | H | 0.38299 | 1.66323 | 4.04037 |
| 186 | C | 1.41747 | 3.05722 | 2.73031 |
| 187 | H | 0.50968 | 3.60992 | 2.47422 |
| 188 | C | 2.64608 | 3.47096 | 2.22005 |
| 189 | C | 3.83443 | 2.79986 | 2.60697 |
| 190 | C | 3.75734 | 1.67447 | 3.4792 |
| 191 | C | 3.46394 | −1.8181 | 5.99876 |
| 192 | H | 2.39412 | −2.05615 | 5.95761 |
| 193 | C | 3.85112 | −1.59233 | 7.46838 |
| 194 | H | 3.29552 | −0.71912 | 7.84675 |
| 195 | H | 4.92896 | −1.37102 | 7.53123 |
| 196 | C | 3.50878 | −2.84698 | 8.28699 |
| 197 | H | 3.80014 | −2.69814 | 9.33947 |
| 198 | H | 2.41431 | −2.99983 | 8.27138 |
| 199 | C | 4.20094 | −4.09169 | 7.71129 |
| 200 | H | 3.91797 | −4.9894 | 8.28462 |
| 201 | H | 5.29578 | −3.97445 | 7.80667 |
| 202 | C | 3.85128 | −4.28512 | 6.22731 |
| 203 | H | 4.39424 | −5.14816 | 5.80902 |
| 204 | H | 2.77095 | −4.46531 | 6.10559 |
| 205 | C | 4.25053 | −3.02538 | 5.44335 |
| 206 | H | 5.3216 | −2.84239 | 5.59663 |
| 207 | C | 5.33903 | −3.2831 | 3.24616 |
| 208 | C | 5.22868 | −3.40071 | 1.76978 |
| 209 | C | 6.38575 | −3.3982 | 0.99255 |
| 210 | H | 7.34595 | −3.2731 | 1.49699 |
| 211 | C | 6.31036 | −3.57876 | −0.40086 |
| 212 | H | 7.20783 | −3.59321 | −1.02265 |
| 213 | C | 5.07664 | −3.76616 | −1.01996 |
| 214 | C | 5.0193 | −4.00862 | −2.48689 |
| 215 | C | 2.53182 | −4.1828 | −2.32396 |
| 216 | C | 2.62756 | −3.99435 | −0.85434 |
| 217 | C | 1.47982 | −4.06608 | −0.06882 |
| 218 | H | 0.52185 | −4.30777 | −0.53585 |
| 219 | C | 1.55328 | −3.8673 | 1.32514 |
| 220 | H | 0.6487 | −3.9466 | 1.93371 |
| 221 | C | 2.77686 | −3.60675 | 1.93838 |
| 222 | C | 2.83804 | −3.3817 | 3.40833 |
| 223 | C | 3.963 | −3.57455 | 1.16112 |
| 224 | C | 3.88814 | −3.76493 | −0.24998 |
| 225 | C | 3.59897 | −4.1513 | −4.53898 |
| 226 | H | 2.5256 | −4.02099 | −4.7223 |
| 227 | C | 4.0129 | −5.51584 | −5.11335 |
| 228 | H | 3.48648 | −6.30576 | −4.55522 |
| 229 | H | 5.09713 | −5.66029 | −4.97922 |
| 230 | C | 3.64494 | −5.5692 | −6.60427 |
| 231 | H | 3.93595 | −6.54395 | −7.02816 |
| 232 | H | 2.54794 | −5.48067 | −6.70681 |
| 233 | C | 4.3186 | −4.42487 | −7.3755 |
| 234 | H | 4.03082 | −4.45289 | −8.43903 |
| 235 | H | 5.41544 | −4.55572 | −7.32939 |
| 236 | C | 3.95467 | −3.05955 | −6.77075 |
| 237 | H | 4.48645 | −2.24906 | −7.29541 |
| 238 | H | 2.87229 | −2.87584 | −6.86247 |
| 239 | C | 4.35465 | −3.0302 | −5.28683 |
| 240 | H | 5.43151 | −3.22655 | −5.21056 |

REFERENCES (1) Terech, P.; Weiss, R. G. *Chem. Rev.* 1997, 97, 3133.
(2) Steed, J. W. *Chem. Commun.* 2011, 47, 1379.
(3) Steed, J. W. *Chem. Soc. Rev.* 2010, 39, 3686.
(4) Frederix, P. W. J. M. et al. *Nat. Chem.* 2015, 7, 30.
(5) van Esch, J. H.; Feringa, B. L. *Angew. Chem. Int. Ed.* 2000, 39, 2263.
(6) George, M.; Weiss, R. G. *Acc. Chem. Res.* 2006, 39, 489.
(7) Raeburn, J. et al. *Chem. Soc. Rev.* 2013, 42, 5143.
(8) Raeburn, J.; Adams, D. *J. Chem. Commun.* 2015, 51, 5170.
(9) Fleming, S.; Ulijn, R. V. *Chem. Soc. Rev.* 2014, 43, 8150.
(10) Weiss, R. G. I *Am. Chem. Soc.* 2014, 136, 7519.
(11) Aggeli, A. et al. N. *Proc. Natl. Acad. Sci. USA* 2001, 98, 11857.
(12) Brizard, A. et al. *Top. Curr. Chem.* 2005, 256, 167.
(13) Edwards, W.; Smith, D. K. I *Am. Chem. Soc.* 2014, 136, 1116.
(14) Jung, J. H. et al. *Am. Chem. Soc.* 2000, 122, 5008.
(15) Smith, D. K. *Chem. Soc. Rev.* 2009, 38, 684.
(16) Morris, K. L. et al. *J. Nat. Commun.* 2013, 4, 1480.

(17) Hasell, T. I Am. Chem. Soc. 2011, 134, 588.
(18) Čaplar, V. et al. M. Chem. Eur. J. 2010, 16, 3066.
(19) Makarević, J. et al. Chem. Eur. J. 2003, 9, 5567.
(20) Watanabe, Y. et al. M. Org. Lett. 2004, 6, 1547.
(21) Borges, A. R. et al. Langmuir 2008, 24, 7421.
(22) Frkanec, L.; inić, M. Chem. Commun. 2010, 46, 522.
(23) Nagy, K. J. et al. J. Am. Chem. Soc. 2011, 133, 14975.
(24) He, Y. et al. Chem. Commun. 2011, 47, 1589.
(25) Shen, Z.; Wang, T.; Liu, M. Langmuir 2014, 30, 10772.
(26) Lin, J. et al. Chem. Commun. 2013, 49, 9320.
(27) Desiraju, G. R. Acc. Chem. Res. 1996, 29, 441.
(28) Hwang, I. et al. Angew. Chem. Int. Ed. 2007, 46, 210.
(29) Park, D. J. et al. Proc. Natl. Acad. Sci. U.S.A. 2015, 112, 977.
(30) Kang, J. et al. Science 2015, 347, 646.
(31) Ajami, D.; Rebek, J. Acc. Chem. Res. 2013, 46, 990.
(32) Ajami, D. et al. Chem. Soc. Rev. 2015, 44, 490.
(33) Liu, S. et al. J. Am. Chem. Soc. 2013, 135, 4314.
(34) Kumari, H. et al. Am. Chem. Soc. 2013, 135, 7110.
(35) Kumari, H. et al. Acc. Chem. Res. 2014, 47, 3080.
(36) Liu, Y. et al. Science 2011, 333, 436.
(37) Beijer, F. H. et al. Angew. Chem. Int. Ed. 1998, 37, 75.
(38) Corbin, P. S.; Zimmerman, S. C. J. Am. Chem. Soc. 1998, 120, 9710.
(39) Lafitte, V. G. H. et al. Am. Chem. Soc. 2006, 128, 6544.
(40) Blight, B. A. et al. Nat. Chem. 2011, 3, 244.
(41) Montenegro, J. et al. Acc. Chem. Res. 2013, 46, 2955.
(42) Hennig, A. et al. Am. Chem. Soc. 2009, 131, 16889.
(43) Fischer, L. et al. Angew. Chem. Int. Ed. 2009, 48, 1625.
(44) Pantoş, G. D. et al. Angew. Chem. Int. Ed. 2007, 46, 194.
(45) Gong, H.-Y. et al. Nat. Chem. 2010, 2, 406.
(46) Nalluri, S. K. M. et al. Angew. Chem. Int. Ed. 2014, 53, 5882.
(47) Ogi, S. et al. J. Am. Chem. Soc. 2015, 137, 3300.
(48) Piana, F. et al. RSC Adv. 2015, 5, 12287.
(49) Kouwer, P. H. J. et al. Nature 2013, 493, 651.
(50) Scheiner, S. Noncovalent Forces 2015, 19, 69.
(51) Schneebeli, S. T. Angew. Chem. Int. Ed. 2013, 52, 13100.
(52) Liu, Z.; Liu, G.; Wu, Y.; Cao, D.; Sun, J.; Schneebeli, S. T.; Nassar, M. S.; Mirkin, C. A.; Stoddart, J. F. J. Am. Chem. Soc. 2014, 136, 16651.
(53) Steiner, T. Chem. Commun. 1997, 727.
(54) Kar, T.; Scheiner, S. J. Phys. Chem. A 2004, 108, 9161.
(55) Aida, T.; Meijer, E. W.; Stupp, S. I. Science 2012, 335, 813.
(56) Wu, X. et al. J. Am. Chem. Soc. 2015, 137, 5879.
(57) Koshkakaryan, G. et al. Chem. Commun. 2010, 46, 8579.
(58) Huang, Z. et al. Science 2012, 337, 1521.
(59) Yamagishi, H. et al. J. Am. Chem. Soc. 2015, 137, 7628.
(60) Ren, C. et al. J. Am. Chem. Soc. 2011, 133, 13930.
(61) Rambo, B. M. et al. Acc. Chem. Res. 2012, 45, 1390.
(62) Meazza, L. et al. Nature Chem. 2012, 5, 42.
(63) Zhang, Z. et al. Angew. Chem. Int. Ed. 2011, 50, 1397.
(64) Steiner, T.; R. Desiraju, G. Chem. Commun. 1998, 891.
(65) Gabutti, S. et al. Chem. Commun. 2008, 2370.
(67) U.S. Pat. Pub. No. 2016/0276669.
(68) Shao, Y. et al. Mol. Phys. 2014, 113, 184.
(69) Perdew, J. P. et al. Phys. Rev. Lett. 1996, 77, 3865.
(70) Grimme, S. J. Comput. Chem. 2006, 27, 1787.

All references, including publications, patent applications, and patents, cited herein are hereby incorporated by reference to the same extent as if each reference were individually and specifically indicated to be incorporated by reference and were set forth in its entirety herein.

What is claimed:

1. A supramolecular assembly comprising a mixture of rigid macrocycles capable of interacting through [C—H . . . O] hydrogen bonds, wherein the mixture of rigid macrocycles comprises a first rigid napthalenediimide-based macrocycle entantiomer and a second rigid napthalenediimide-based macrocycle enantiomer.

2. The supramolecular assembly of claim 1, wherein the mixture is a racemic mixture of the first rigid macrocycle enantiomer and the second rigid macrocycle enantiomer.

3. The supramolecular assembly of claim 1, wherein the first rigid macrocycle enantiomer is a first rigid triangular macrocycle enantiomer and the second rigid macrocycle enantiomer is a second rigid triangular macrocycle enantiomer.

4. The supramolecular assembly of claim 1, wherein the first rigid napthalenediimide-based macrocycle enantiomer is the compound of:

Formula (I)

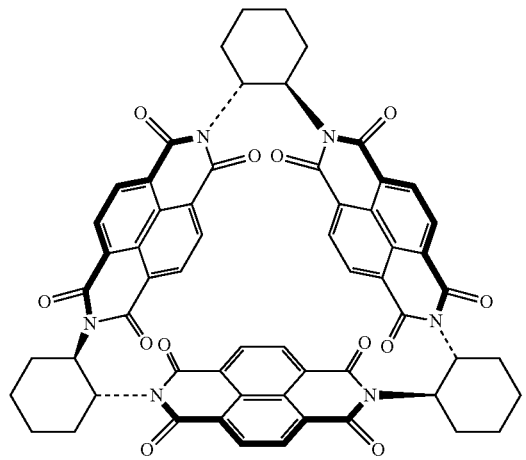

and the second rigid napthalenediimide-based macrocycle enantiomer is a compound of:

Formula (II)

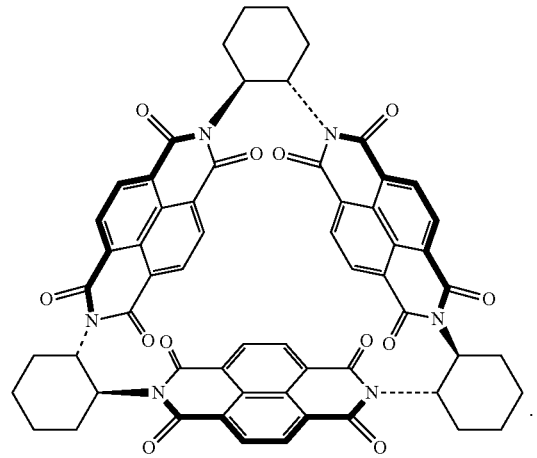

5. The supramolecular assembly of claim 1, wherein the first rigid macrocycle enantiomer cooperatively interacts with the second rigid macrocycle enantiomer through [C—H . . . O] hydrogen bonds.

6. The supramolecular assembly of claim 1, wherein the supramolecular assembly is a gel.

7. The supramolecular assembly of claim 1, wherein the supramolecular assembly is a precipitate.

8. The supramolecular assembly of claim 1 wherein the supramolecular assembly has a fibrillar morphology or a needle morphology.

9. The supramolecular assembly of claim 1, wherein the supramolecular assembly has a high-aspect ratio.

10. The supramolecular assembly of claim 1, wherein the supramolecular assembly has a first dimension of less than about 3 nm and a second dimension of greater than about 100 nm.

11. The supramolecular assembly of claim 1, wherein the first rigid macrocycle enantiomer and the second rigid macrocycle enantiomer coaxially stack in an alternating fashion.

12. A method for preparing a supramolecular assembly, the method comprising providing a mixture of rigid macrocycles capable of interacting through [C—H . . . O] hydrogen bonds, the mixture of rigid macrocycles comprising a first rigid napthalenediimide-based macrocycle enantiomer and a second rigid napthalenediimide-based macrocycle enantiomer, and providing a solvent.

13. The method of claim 12, wherein the mixture of rigid macrocycles is an equimolar mixture of the first rigid macrocycle and the second rigid macrocycle.

14. The method of claim 12, wherein providing the mixture of rigid macrocycles comprises mixing a first solution, the first solution comprising the first rigid macrocycle, and a second solution, the second solution comprising the second rigid macrocycle.

15. The method of claim 12, wherein providing the mixture of rigid macrocycles comprises dissolving the first rigid macrocycle and/or the second rigid macrocycle.

16. The method of claim 12, wherein the solvent is a halogenated alkane.

17. A battery comprising the supramolecular assembly as in claim 1.

18. The battery of claim 17, wherein the battery is a lithium battery.

19. The method of claim 12, wherein the first rigid napthalenediimide-based macrocycle enantiomer is the compound of:

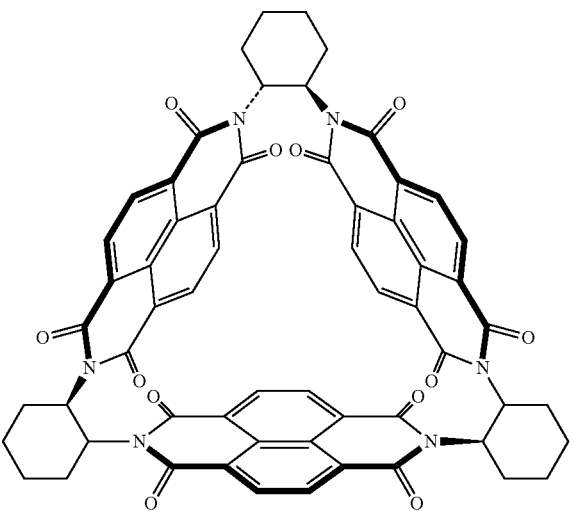

Formula (I)

and the second rigid napthalenediimide-based macrocycle enantiomer is a compound of:

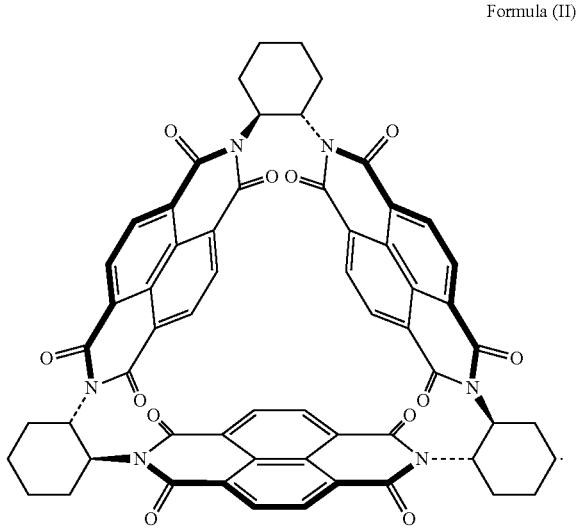

Formula (II)

20. The battery of claim 17, wherein the first rigid napthalenediimide-based macrocycle enantiomer is the compound of:

Formula (I)
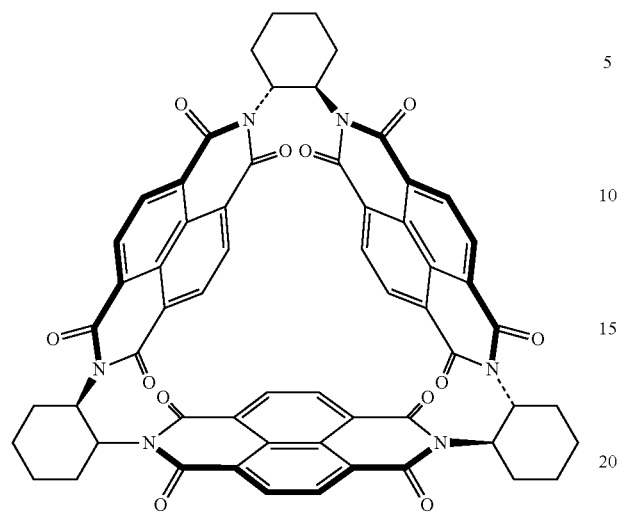
and the second rigid napthalenediimide-based macrocycle enantiomer is a compound of:
Formula (II)
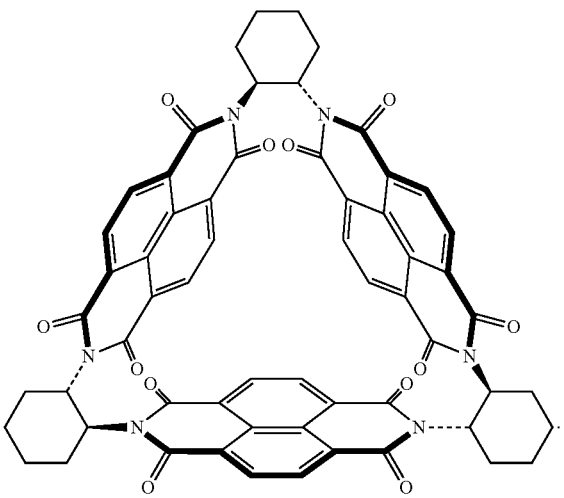
* * * * *

UNITED STATES PATENT AND TRADEMARK OFFICE
CERTIFICATE OF CORRECTION

PATENT NO. : 10,745,418 B2  
APPLICATION NO. : 16/069940  
DATED : August 18, 2020  
INVENTOR(S) : James Fraser Stoddart and Zhichang Liu Page 1 of 1

It is certified that error appears in the above-identified patent and that said Letters Patent is hereby corrected as shown below:

In the Claims

Column 28, Line 6, "entantiomer" should be --enantiomer--.

Signed and Sealed this  
Seventeenth Day of August, 2021

Drew Hirshfeld  
*Performing the Functions and Duties of the*  
*Under Secretary of Commerce for Intellectual Property and*  
*Director of the United States Patent and Trademark Office*